US008191339B2

(12) United States Patent
Tribble et al.

(10) Patent No.: US 8,191,339 B2
(45) Date of Patent: Jun. 5, 2012

(54) AUTOMATED DRUG PREPARATION APPARATUS INCLUDING AUTOMATED DRUG RECONSTITUTION

(75) Inventors: Dennis Tribble, Ormond Beach, FL (US); Joel A. Osborne, Port Orange, FL (US); Abdul Wahid Khan, Lindenhurst, IL (US); Edward J. Lefebre, Port Orange, FL (US)

(73) Assignee: FHT, Inc., Englewood, CO (US)

( * ) Notice: Subject to any disclaimer, the term of this patent is extended or adjusted under 35 U.S.C. 154(b) by 122 days.

(21) Appl. No.: 12/708,841

(22) Filed: Feb. 19, 2010

(65) Prior Publication Data

US 2010/0217431 A1    Aug. 26, 2010

Related U.S. Application Data

(63) Continuation of application No. 11/555,577, filed on Nov. 1, 2006, now Pat. No. 7,753,085, which is a continuation-in-part of application No. 11/434,850, filed on May 15, 2006, now Pat. No. 7,240,699, which is a continuation of application No. 10/728,371, filed on Dec. 3, 2003, now Pat. No. 7,117,902.

(60) Provisional application No. 60/430,481, filed on Dec. 3, 2002, provisional application No. 60/470,328, filed on May 13, 2003.

(51) Int. Cl.
*B65B 3/00* (2006.01)
(52) U.S. Cl. ............... 53/281; 53/287; 53/468; 53/478; 53/485
(58) Field of Classification Search .............. 53/281, 53/287, 468, 471, 478, 485
See application file for complete search history.

(56) References Cited

U.S. PATENT DOCUMENTS

| 2,880,723 A | 4/1959 | Adams |
| 2,981,432 A | 4/1961 | Flood |
| 2,988,984 A | 6/1961 | Eckert |
| 3,002,387 A | 10/1961 | Micheletti |
| 3,200,486 A | 8/1965 | Shields |
| 3,527,017 A | 9/1970 | Taylor et al. |
| 3,556,342 A | 1/1971 | Guarr |
| 3,736,933 A | 6/1973 | Szabo |
| 3,823,818 A | 7/1974 | Shaw |
| 3,835,897 A | 9/1974 | Gess |
| 3,848,485 A | 11/1974 | Grenci |
| 3,865,236 A | 2/1975 | Rycroft |
| 3,880,211 A | 4/1975 | Gess |
| 3,965,945 A | 6/1976 | Ross |
| 4,058,121 A | 11/1977 | Choksi et al. |
| 4,372,464 A | 2/1983 | Otten |

(Continued)

FOREIGN PATENT DOCUMENTS

GB            2259081         3/1993

(Continued)

*Primary Examiner* — Hemant M Desai
(74) *Attorney, Agent, or Firm* — Leason Ellis LLP

(57) ABSTRACT

An automated medication preparation system for preparing a prescribed dosage of medication in a drug delivery device includes a plurality of stations for receiving, handling and processing the drug delivery device so that the prescribed dosage of medication is delivered to the drug delivery device and a transporting device that receives and holds more than one drug delivery device and moves the drug delivery devices in a controlled manner from one station to another station. The system is configured so that two or more separate drug delivery devices can be acted upon at the same time.

29 Claims, 18 Drawing Sheets

U.S. PATENT DOCUMENTS

| | | |
|---|---|---|
| 4,472,357 A | 9/1984 | Levy et al. |
| 4,502,616 A | 3/1985 | Meierhoefer |
| 4,512,475 A | 4/1985 | Federighi et al. |
| 4,624,148 A | 11/1986 | Averette |
| 4,639,250 A | 1/1987 | Rycroft |
| 4,669,599 A | 6/1987 | Dijkmeijer et al. |
| 4,674,652 A | 6/1987 | Aten et al. |
| 4,699,186 A | 10/1987 | Palin et al. |
| 4,706,207 A | 11/1987 | Hennessy et al. |
| 4,758,230 A | 7/1988 | Rycroft |
| 4,773,285 A | 9/1988 | Dionne et al. |
| 4,835,707 A | 5/1989 | Amano et al. |
| 4,847,764 A | 7/1989 | Halvorson |
| 4,861,335 A | 8/1989 | Reynolds et al. |
| 4,865,592 A | 9/1989 | Rycroft |
| 4,878,705 A | 11/1989 | Arnquist |
| 4,944,736 A | 7/1990 | Holtz |
| 5,004,962 A | 4/1991 | Fonss et al. |
| 5,040,437 A | 8/1991 | Mueller |
| 5,229,074 A | 7/1993 | Heath et al. |
| 5,256,154 A | 10/1993 | Liebert et al. |
| 5,288,285 A | 2/1994 | Carter |
| 5,324,519 A | 6/1994 | Dunn et al. |
| 5,341,854 A | 8/1994 | Zezulka et al. |
| 5,356,393 A | 10/1994 | Haber et al. |
| 5,363,885 A | 11/1994 | McConnell et al. |
| 5,366,896 A * | 11/1994 | Margrey et al. ............. 436/48 |
| 5,411,489 A | 5/1995 | Pagay et al. |
| 5,431,201 A | 7/1995 | Torchia et al. |
| 5,451,528 A | 9/1995 | Raymoure et al. |
| 5,479,969 A | 1/1996 | Hardie et al. |
| 5,496,288 A | 3/1996 | Sweeney |
| 5,522,512 A | 6/1996 | Archer et al. |
| 5,522,804 A | 6/1996 | Lynn |
| 5,542,935 A | 8/1996 | Unger et al. |
| 5,597,530 A | 1/1997 | Smith et al. |
| 5,651,775 A | 7/1997 | Walker et al. |
| 5,669,599 A | 9/1997 | Toh et al. |
| 5,704,921 A | 1/1998 | Carilli |
| 5,735,181 A | 4/1998 | Anderson |
| 5,769,086 A | 6/1998 | Ritchart et al. |
| 5,797,515 A | 8/1998 | Liff et al. |
| 5,805,454 A | 9/1998 | Valerino, Sr. et al. |
| 5,826,409 A | 10/1998 | Slepicka et al. |
| 5,855,839 A | 1/1999 | Brunel et al. |
| 5,884,457 A | 3/1999 | Ortiz et al. |
| 5,895,019 A | 4/1999 | Ibarra |
| 5,899,889 A | 5/1999 | Futagawa et al. |
| 5,911,252 A | 6/1999 | Cassel |
| 5,948,360 A | 9/1999 | Rao et al. |
| 6,027,472 A | 2/2000 | Kriesel et al. |
| 6,048,086 A | 4/2000 | Valerino |
| 6,068,614 A | 5/2000 | Kimber et al. |
| 6,082,987 A | 7/2000 | Su et al. |
| 6,142,039 A | 11/2000 | Herring, Sr. |
| 6,200,289 B1 | 3/2001 | Hochman et al. |
| 6,249,717 B1 | 6/2001 | Nicholson |
| 6,256,964 B1 * | 7/2001 | Drevfors ............. 53/426 |
| 6,343,690 B1 | 2/2002 | Britton et al. |
| 6,360,794 B1 | 3/2002 | Turner |
| 6,599,476 B1 | 7/2003 | Watson et al. |
| 6,623,455 B2 | 9/2003 | Small et al. |
| 6,813,868 B2 | 11/2004 | Baldwin et al. |
| 6,857,250 B1 * | 2/2005 | Taylor ............. 53/331 |
| 6,915,823 B2 | 7/2005 | Osborne et al. |
| 7,017,622 B2 * | 3/2006 | Osborne et al. ............. 141/27 |
| 7,059,104 B2 * | 6/2006 | Taylor ............. 53/471 |
| 7,163,035 B2 | 1/2007 | Khan et al. |
| 7,240,699 B2 | 7/2007 | Osborne |
| 7,260,447 B2 | 8/2007 | Osborne |
| 7,343,943 B2 | 3/2008 | Khan et al. |
| 7,484,345 B2 * | 2/2009 | Woods et al. ............. 53/381.4 |
| 2001/0018937 A1 | 9/2001 | Nemoto |
| 2002/0035412 A1 | 3/2002 | Kircher et al. |
| 2004/0250842 A1 | 12/2004 | Adams et al. |
| 2006/0178578 A1 | 8/2006 | Tribble et al. |
| 2007/0043767 A1 | 2/2007 | Osborne et al. |
| 2008/0169043 A1 | 7/2008 | Tribble et al. |
| 2008/0169044 A1 | 7/2008 | Osborne et al. |
| 2008/0169045 A1 | 7/2008 | Tribble et al. |
| 2008/0169046 A1 | 7/2008 | Bender et al. |
| 2010/0108181 A1 * | 5/2010 | Westner et al. ............. 141/4 |

FOREIGN PATENT DOCUMENTS

| | | |
|---|---|---|
| WO | WO 90/09776 | 9/1990 |
| WO | WO 99/28724 | 6/1999 |

* cited by examiner

FIG. 10
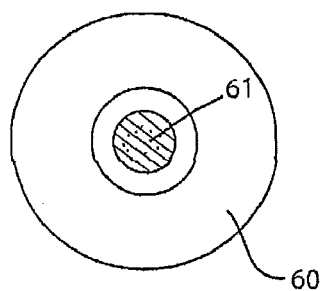
FIG. 12
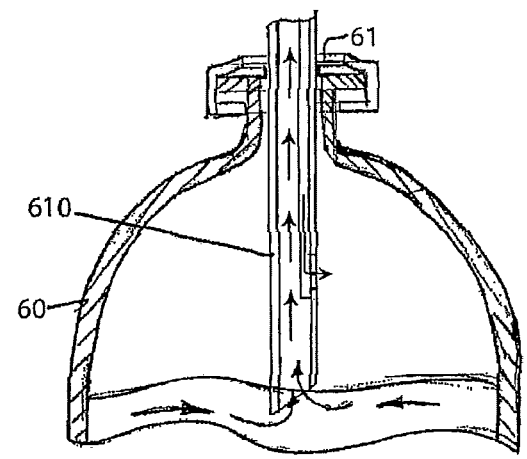
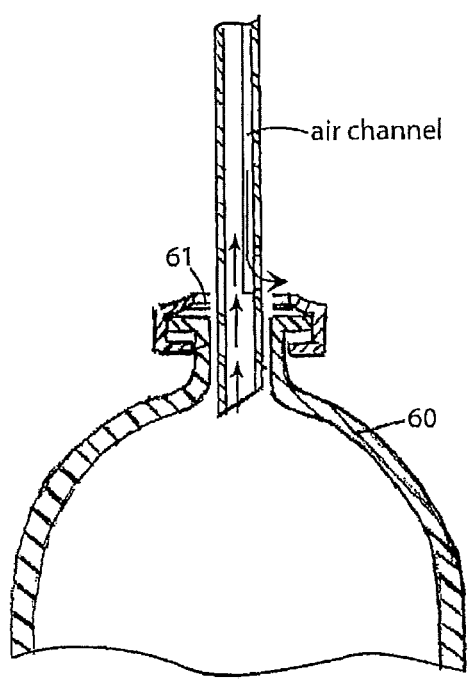
FIG. 11

◎ loaded syringe　　◎ loaded syringe active

FIG. 16

Entry of Diluted Product 1100

| | Container | Drug |

1101 Add Product

Vial Information
- Description: Oxacillin 100mg — 1102
- Container: Oxacillin 10mg
- Drug Code: 1234567890 — 1104
- Barcode: 1234567890 — 1106
- Reconstituted Volume (mL): 10 — 1107
- Reconstituted Concentration: 10mg/mL
- Reconstituted Specific Gravity g/mL: 1 — 1108
- Product % Variance: 0 | 0
- Quarantine % Variance: 0 | 0
- Vial Width (mm): 1
- Vial Height (mm): 1
- Neck Hieght (mm): 1
- Septum Distance (mm):
- Vent Volume (mL): 1

Multi Dose ☐    Dilution ☐

Reconstitution Information
- Reconstitution Volume (mL):
- Agitation Time (s):
- Expriration Time (hours): 1
- Min. Residual Volume (mL): 1

Order Information
- Price:
- Wholesaler ID:
- Minimum Order Quanitity:

ForHealth

Add | Cancel

AUTOMATED DRUG PREPARATION APPARATUS INCLUDING AUTOMATED DRUG RECONSTITUTION

CROSS-REFERENCE TO RELATED APPLICATIONS

This application is a continuation of U.S. patent application Ser. No. 11/555,577, filed Nov. 1, 2006 now U.S. Pat. No. 7,753,085 issued on Jul. 13, 2010, which is a continuation-in-part of U.S. patent application Ser. No. 11/434,850, filed May 15, 2006 now U.S. Pat. No. 7,240,699 issued on Jul. 10, 2007, which is a continuation of U.S. patent application Ser. No. 10/728,371, filed Dec. 3, 2003 now U.S. Pat. No. 7,117,902, issued on Oct. 10, 2006, which claims the benefit of U.S. patent application Ser. No. 60/430,481, filed Dec. 3, 2002 and U.S. patent application Ser. No. 60/470,328, filed May 13, 2003, each of which is hereby incorporated by reference in its entirety.

TECHNICAL FIELD

The present invention relates generally to medical and pharmaceutical equipment, and more particularly, to an automated system for preparing a drug delivery device, such as a syringe, to receive a unit dose of medication and then dispensing the unit dose of medication into the drug delivery device (e.g., a syringe) and to a number of safety and control features that preserve the integrity and optimize the performance and capabilities of the system.

BACKGROUND

Disposable syringes are in widespread use for a number of different types of applications. For example, syringes are used not only to withdraw a fluid (e.g., blood) from a patient but also to administer a medication to a patient. In the latter, a cap or the like is removed from the syringe and a unit dose of the medication is carefully measured and then injected or otherwise disposed within the syringe.

As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume.

In some instances, the medication that is to be delivered to the patient includes more than one pharmaceutical substance. For example, the medication can be a mixture of several components, such as several pharmaceutical substances.

By automating the medication preparation process, increased production and efficiency are achieved and better environmental control of the production process is achieved, thereby reducing opportunities for contamination. This results in reduced production costs and also permits the system to operate over any time period of a given day with only limited operator intervention for manual inspection to ensure proper operation is being achieved. Such a system finds particular utility in settings, such as large hospitals, where a large number of doses of medications that must be prepared daily. Traditionally, these doses have been prepared manually in what is an exacting but tedious responsibility for a highly skilled staff. In order to be valuable, automated systems must maintain the exacting standards set by medical regulatory organizations, while at the same time simplifying the overall process and reducing the time necessary for preparing the medications.

Because syringes are used often as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a vial that is sealed with a safety cap or the like. In conventional medication preparation, a trained person retrieves the correct vial from a storage cabinet or the like, confirms the contents and then removes the safety cap manually. This is typically done by simply popping the safety cap off with one's hands. Once the safety cap is removed, the trained person inspects the integrity of the membrane and cleans the membrane. An instrument, e.g., a needle, is then used to pierce the membrane and withdraw the medication contained in the vial. The withdrawn medication is then placed into a syringe to permit subsequent administration of the medication from the syringe.

All injections must be administered as liquids. If an injectable substance has a limited shelf-life as a liquid, it may be provided in solid or powdered for to be liquefied with a diluent, such as water or saline, prior to use. The process is called reconstitution and involves selecting an appropriate diluent, injecting the measured volume of diluent into the vial, and agitating the vial to ensure complete dissolution of the drug. The medication thus initially comes in a solid form and is contained in an injectable drug vial and then the proper amount of diluent is added and the vial is agitated to ensure that all of the solid goes into solution, thereby providing a medication having the desired concentration. The drug vial is typically stored in a drug cabinet or the like and is then delivered to other stations where it is processed to receive the diluent. This is a time consuming process and is open to human error in the reconstitution of the medication.

What is needed in the art and has heretofore not been available is a system and method for automating the medication preparation process and more specifically, an automated system and method for preparing a syringe including preparing and filling the syringe with reconstituted medication, as well as a number of safety features that improve the integrity of the process.

SUMMARY

An automated medication preparation system for preparing a prescribed dosage of medication in a drug delivery device includes a plurality of stations for receiving, handling and processing the drug delivery device so that the prescribed dosage of medication is delivered to the drug delivery device and a transporting device that receives and holds more than one drug delivery device and moves the drug delivery devices in a controlled manner from one station to another station. The system is configured so that two or more separate drug delivery devices can be acted upon at the same time.

In another aspect, an automated drug preparation system for preparing a prescribed dosage of medication in a syringe includes a first drug delivery station that includes a first automated drug delivery device that is in fluid communication with a source of a first fluid that is for delivery to the syringe. The system further includes an adjustable plunger extension mechanism that includes a movable component that intimately engages a plunger of the syringe so that a first movement of the movable component is translated into a first extension of the plunger a first defined distance which causes a first volume of the first fluid to be drawn into the syringe.

The system also includes a controller that includes stored medication orders including a final volume and concentration of the prescribed dosage of medication, wherein and based on the stored medication orders, the controller calculates the first defined distance that the plunger is moved to draw the first volume of the first fluid and causes the plunger to extend the first defined distance. When the first volume is less than the final volume, the controller calculates the difference between the final volume and the first volume and disengages the fluid communication between the source of the first fluid and the first automated drug delivery device and then calculates a second defined distance the plunger is to be moved to permit reception of a second volume of a second fluid and causes the plunger to extend the second defined distance. The sum of the first and second volumes is equal to the final volume.

In another embodiment, a method for processing a drug order and preparing a diluted child drug product from a parent drug product, when it is required, includes the steps of: (a) receiving and processing the drug order and determining whether a diluted child drug product is required as is the case when the drug order can not be prepared by processing the parent drug product; (b) determining whether a diluted parent drug product exists and if none exists, then determining whether an amount of reconstituted parent drug product can be aspirated into a syringe and an amount of diluent directly added to the syringe to yield the diluted child drug product; and if so, then performing these operations; and (c) if the diluted parent drug product exists, then determining whether an amount of the diluted parent drug product can be aspirated into a syringe and an amount of diluent directly added to the syringe to yield the diluted child drug product; and if so, then performing these operations; and if the diluted parent drug product does not exist, then the parent drug product is located and an amount of the parent drug product is aspirated into an empty container and an amount of diluent is added to the container which is then manipulated to produce the child drug product.

In another aspect, a method of preparing a diluted dosage of medication with an automated drug preparation system includes the steps of: (a) reconstituting medication in a first vial, in an automated manner, to produce reconstituted medication have a first concentration which is greater than an inputted target concentration of the dosage of medication; (b) loading a syringe onto a device that controllably delivers the loaded syringe from one station to another station; (c) fluidly connecting the syringe to a source of diluent; (d) extending a plunger of the syringe a predetermined distance to draw a first volume of the diluent into the syringe; and (e) advancing the partially filled syringe to another station where a predetermined amount of the reconstituted medication is delivered to the partially filled syringe to produce the dosage of medication that has a concentration at least about equal to the inputted target concentration, wherein the reconstituted medication is delivered to the partially filled syringe in a manner different than drawing fluid by extension of the syringe plunger.

In yet another embodiment, a method of withdrawing a precise amount of drug from a drug vial in an automated manner includes the steps of: (a) identifying the type of drug vial being used; (b) accessing a database to retrieve stored vial characteristics that are associated with the identified drug vial; (c) positioning a vented cannula relative to the drug vial based on the stored vial characteristics such that in a first mode of operation, a vent port of the vented cannula is open and the drug vial is vented to atmosphere and in a second mode of operation, the vent port is closed; and (d) drawing the precise amount of drug from the drug vial.

Further aspects and features of the exemplary automated drug reconstitution system and method disclosed herein can be appreciated from the appended Figures and accompanying written description.

BRIEF DESCRIPTION OF THE DRAWINGS

FIG. 10 is a top plan view of a drug vial;

FIG. 11 is a cross-sectional view of a drug vial with a vented cannula in a first position where the vent is inactive;

FIG. 12 is a cross-sectional view of a drug vial with the vented cannula in a second position where the vent is active;

FIG. 16 is a computer screen image of an input page for entering information related to a drug dilution order;

DETAILED DESCRIPTION OF PREFERRED EMBODIMENTS

Figure 1:
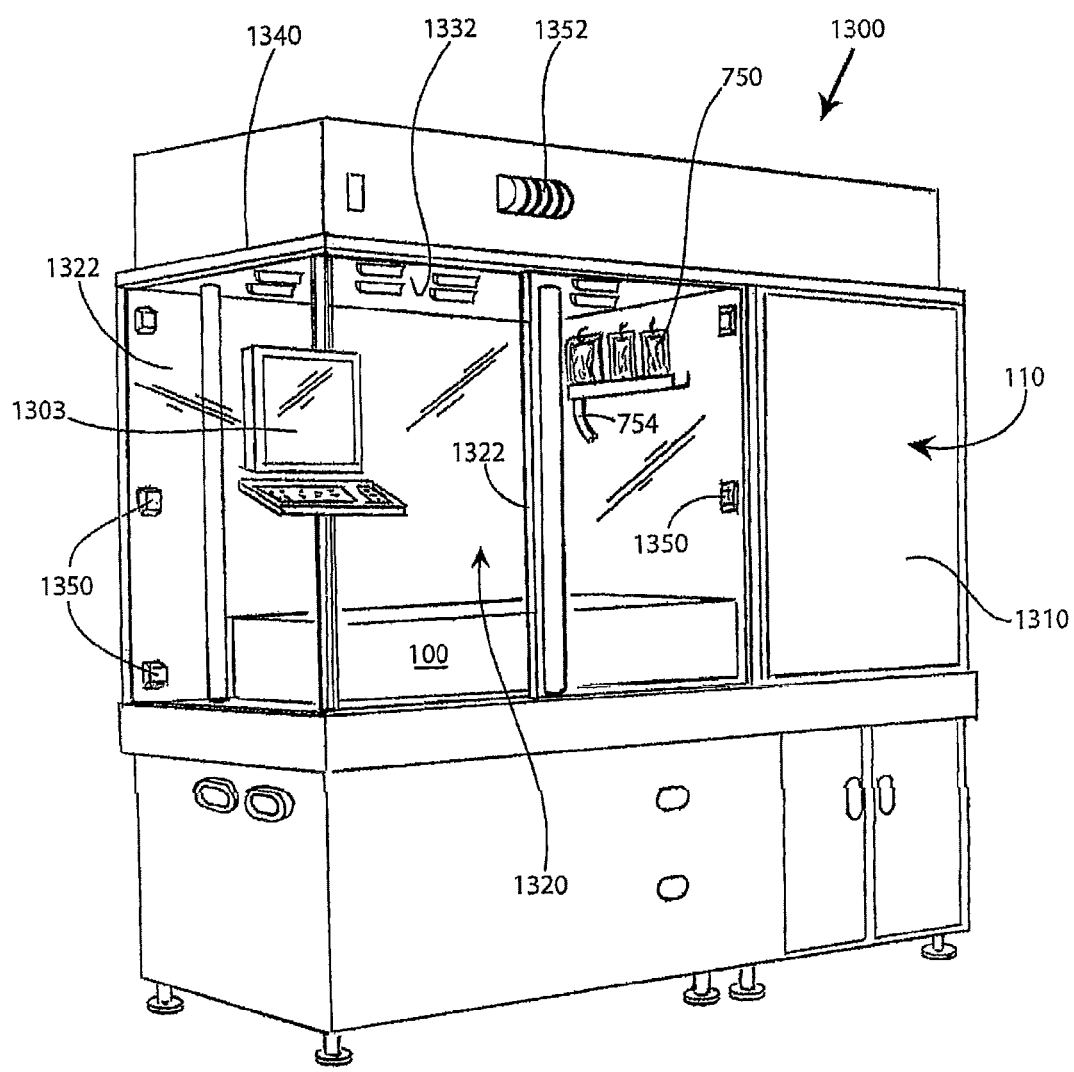
FIG. 1 is a perspective view of a housing that contains an automated drug delivery system that prepares a dosage of medication to be administered to a patient.

FIG. 1 is perspective view of a housing 1300 that is constructed to house an automated drug preparation and delivery system 100 in a sealed, controlled environment when the housing structure is closed (sealed). A user interface, such as a computer, 1303 is provided to permit an operator not only to enter information, such as drug orders, but also to monitor the progress and operation of the system 100. The housing 1300 and its components are described in greater detail below.

Figure 2:
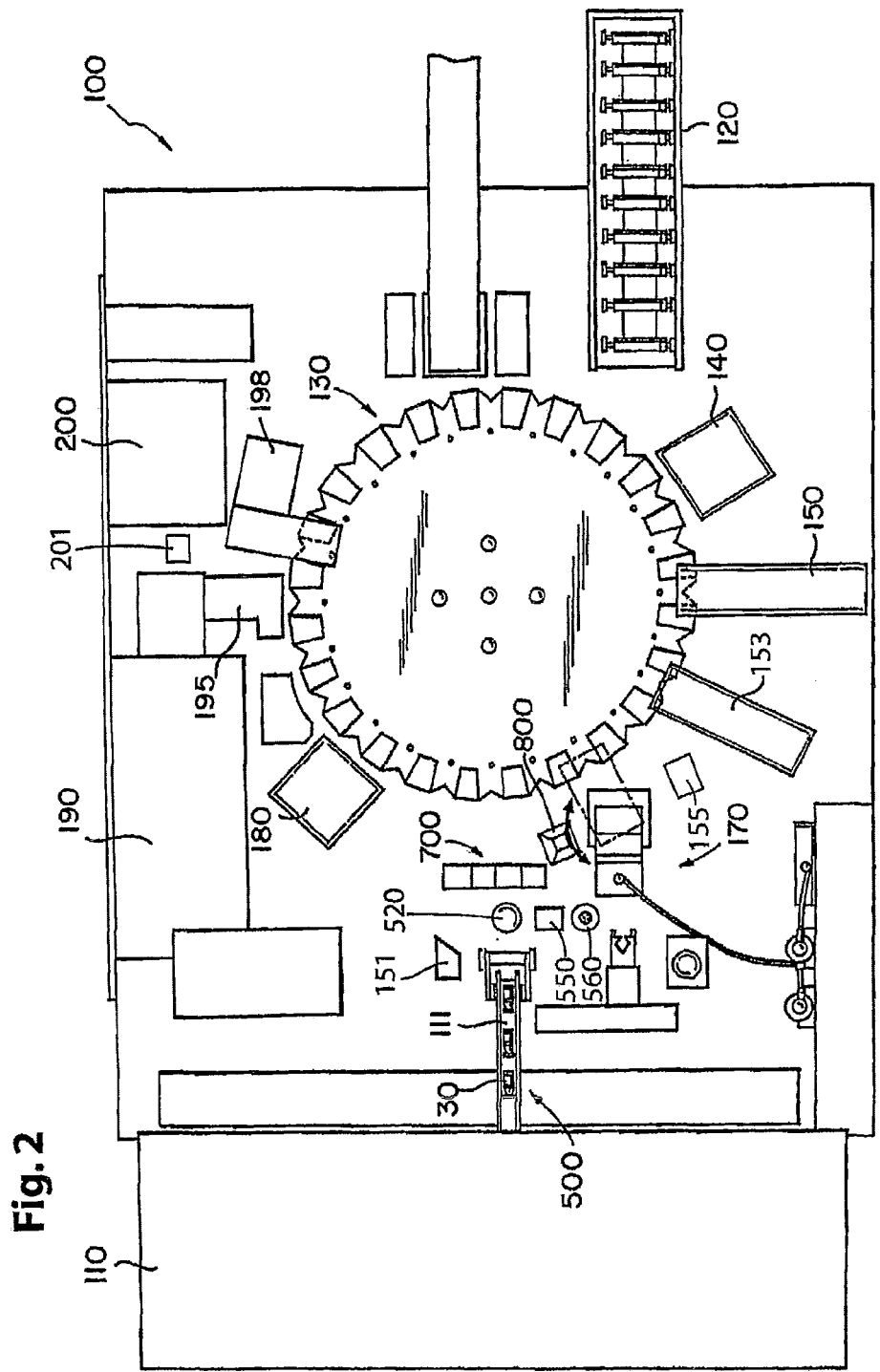
FIG. 2 is a diagrammatic plan view of the automated system for preparing a medication to be administered to a patient.

FIG. 2 is a schematic diagram illustrating one exemplary automated system, generally indicated at 100, for the preparation of a medication. The automated system 100 is divided into a number of stations where a specific task is performed based on the automated system 100 receiving user input instructions, processing these instructions and then preparing unit doses of one or more medications in accordance with the instructions. The automated system 100 includes a station 110 where medications and other substances used in the preparation process are stored. As used herein, the term "medication" refers to a medicinal preparation for administration to a patient. Often, the medication is initially stored as a solid, e.g., a powder, to which a diluent is added to form a medicinal composition. Thus, the station 110 functions as a storage unit for storing one or medications, etc., under proper storage conditions. Typically, medications and the like are stored in sealed containers, such as vials, that are labeled to clearly indicate the contents of each vial. The vials are typically stored in columns and further, empty vials can be stored in one column. The station 110 includes a mechanism that permits the controlled discharge of a selected drug vial 60.

A first station 120 is a syringe storage station that houses and stores a number of syringes. For example, up to 500 syringes or more can be disposed in the first station 120 for storage and later use. The first station 120 can be in the form of a bin or the like or any other type of structure than can hold a number of syringes. In one exemplary embodiment, the syringes are provided as a bandolier structure that permits the syringes to be fed into the other components of the system 100 using standard delivery techniques, such as a conveyor belt, etc.

The system 100 also includes an apparatus 130 for advancing the fed syringes from and to various stations of the system 100. The apparatus 130 can be a rotary device, as shown, or it can be a linear apparatus, or it can assume some other shape. For purposes of illustration only, the apparatus 130 is discussed and shown as being a rotary device; however, it is not limited to such a configuration and therefore, the present disclosure is not limiting of the scope of the present invention.

A number of the stations are arranged circumferentially around the rotary apparatus 130 so that the syringe is first loaded at the first station 120 and then rotated a predetermined distance to a next station, etc., as the medication preparation process advances. At each station, a different operation is performed with the end result being that a unit dose of medication is disposed within the syringe that is then ready to be administered.

One exemplary type of rotary apparatus 130 is a multiple station cam-indexing dial that is adapted to perform material handling operations. The indexer is configured to have multiple stations positioned thereabout with individual nests for each station position. One syringe is held within one nest using any number of suitable techniques, including opposing spring-loaded fingers that act to clamp the syringe in its respective nest. The indexer permits the rotary apparatus 130 to be advanced at specific intervals.

At a second station 140, the syringes are loaded into one of the nests or the like of the rotary apparatus 130. One syringe is loaded into one nest of the rotary apparatus 130 in which the syringe is securely held in place. The system 100 preferably includes additional mechanisms for preparing the syringe for use, such as removing a tip cap and extending a plunger of the syringe at a third station 150 as described below. At this point, the syringe is ready for use.

The system 100 also preferably includes a reader 151 that is capable of reading a label disposed on the sealed container containing the medication. The label is read using any number of suitable reader/scanner/camera devices 151, such as a bar code reader, etc., so as to confirm that the proper medication has been selected from the storage unit of the station 110. Multiple readers can be employed in the system at various locations to confirm the accuracy of the entire process. Once the system 100 confirms that the sealed container (drug vial 60) that has been selected contains the proper medication, the vial 60 is delivered to a station 550 using an automated mechanism, such a robotic gripping device, as will be described in greater detail. At the station 550, the vial 60 is prepared by removing the safety cap from the sealed container and then cleaning the exposed end of the vial. Preferably, the safety cap is removed on a deck of the automated system 100 having a controlled environment. In this manner, the safety cap is removed just-in-time for use. Exemplary vial cap removal devices are disclosed in U.S. Pat. No. 6,604,903, which is hereby expressly incorporated by reference in its entirety. In addition, the vial cap can be removed by other devices, such as one which has a member with suction (vacuum) capabilities incorporated therein for removing the cap. In this embodiment, the suction member is applied to the vial cap and then the suction is activated and then the robotic arm that is gripping and hold the vial body itself is twisted while the drug vial cap is under suction, thus prying the cap from its seal. The cap is still held by suction on the member until the suction is released at which time the cap falls into a trash bin.

The system 100 also preferably includes a fourth station (fluid transfer station) 170 for injecting or delivering a diluent into the medication contained in the sealed container and then subsequently mixing the medication and the diluent to form the medication composition that is to be disposed into the prepared syringe. Alternatively, the station 170 can controllably deliver a predetermined dosage of pre-made medication. At this fluid transfer station 170, the prepared medication composition is withdrawn from the container (i.e., vial) and is then delivered into the syringe. For example, a cannula can be inserted into the sealed vial and the medication composition then aspirated into a cannula set. The cannula is then withdrawn from the vial and is then rotated relative to the rotary apparatus 130 so that it is in line with (above, below, etc.) the syringe. The unit dose of the medication composition is then delivered to the syringe, as well as additional diluent, if necessary or desired. This is referred to as a vial mode of operation where reconstitution of a drug is performed. The tip cap is then placed back on the syringe at a station 180. A station 190 prints and station 195 applies a label to the syringe and a device, such as a reader, can be used to verify that this label is placed in a correct location and the printing thereon is readable. Also, the reader can confirm that the label properly identifies the medication composition that is contained in the syringe and thus performs a safety check. The syringe is then unloaded from the rotary apparatus 130 at an unloading station 200 and delivered to a predetermined location, such as a new order bin, a conveyor, a sorting device, or a reject bin. The delivery of the syringe can be accomplished using a standard conveyor or other type of apparatus. If the syringe is provided as a part of the previously-mentioned syringe bandolier, the bandolier is cut prior at a station 198 located prior to the unloading station 200.

It will be appreciated that an initial labeling station 153 prior to the drug delivery station 170 (e.g., a station right after the load station 120) can be provided for applying a label with a unique identifier, such as a barcode, that uniquely identifies the syringe so that it can be tracked at any location as it is advanced from one station to another station. In other words, a reader 155 downstream of the initial labeling station 153 reads the unique identifier and associates the unique identifier with this particular syringe 10. This permits each drug order to be assigned one particular uniquely identified syringe which is logged into and tracked by the computer. As the syringe is advanced, its location can be tracked by the unique identifier.

A robotic device is provided for moving objects relative to the transporter device (dial 130) and in particular, the robotic device can deliver and/or remove objects, such as the syringe 10 or the drug vials 60, relative to the dial 130. The robotic device thus typically has a gripper mechanism, such as a pair of grippers, for grasping and holding the object.

FIGS. 2-5 illustrate parts of the third station 150 for preparing a syringe 10, the fluid transfer station 170, and the station 180 for preparing the syringe for later use. As is known, a conventional syringe 10 includes a barrel 20 into which fluid is injected and contained and at a barrel tip, a cap 40 is provided to close off the barrel 20. A plunger 50 is slidingly received within the barrel 20 for both drawing fluid into the barrel and discharging fluid therefrom.

Figure 3:
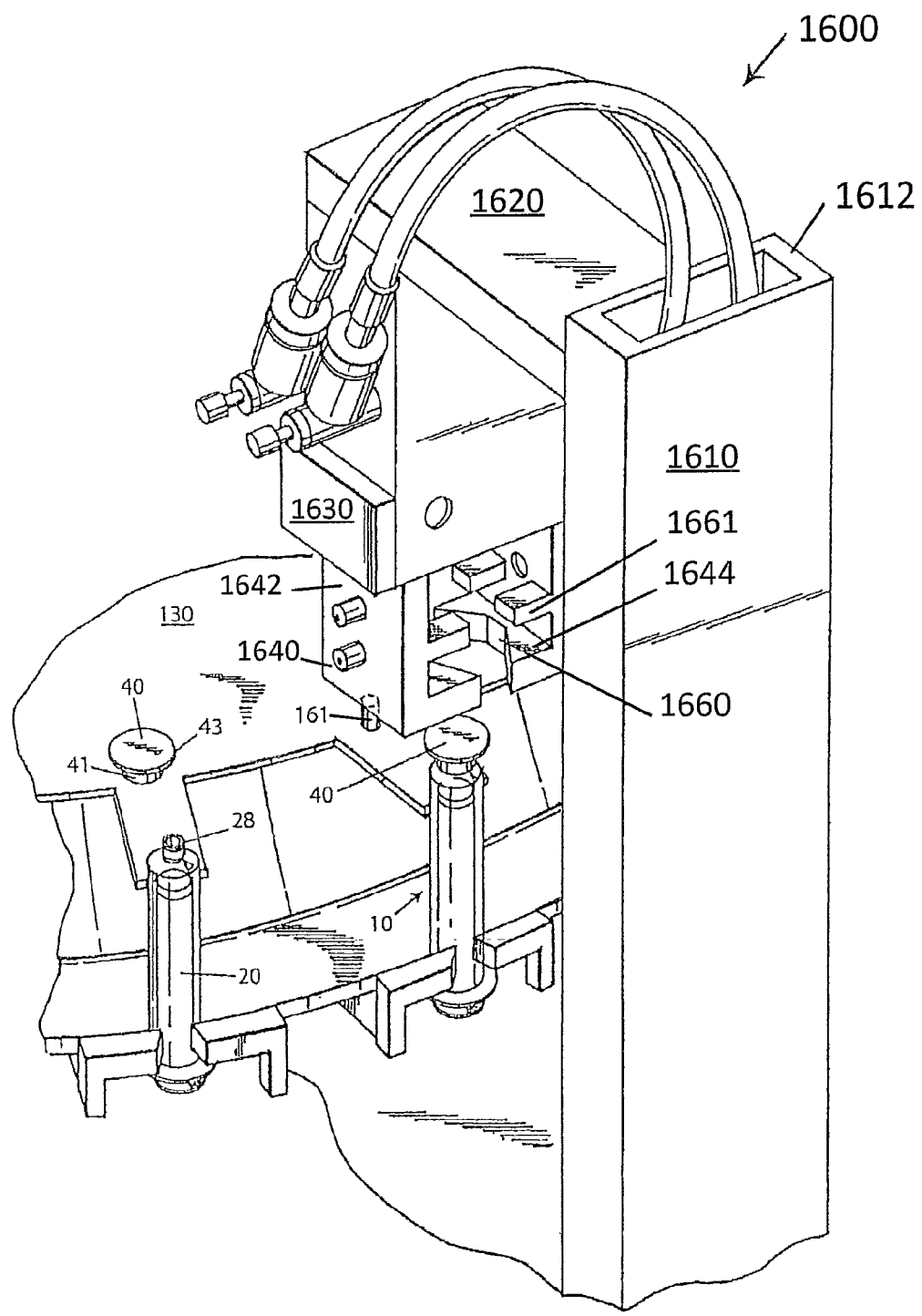
FIG. 3 is a local perspective view of an automated device for removing or replacing the safety tip cap from the syringe.

FIGS. 2-5 thus illustrate in more detail the stations and automated devices that are used in removal of the tip cap 40 from the barrel tip, the filling of barrel chamber with medication and the replacement of the tip cap 40 on the barrel tip. FIG. 3 is a perspective view of an automated device 300 at station 150 that removes the tip cap 40 from the barrel tip as the syringe 10 is prepared for receiving a prescribed dose of medication at station 170 of the automated medication preparation system 100. The device 300 is a controllable device that is operatively connected to a control unit, such as a computer, which drives the device 300 to specific locations at selected times. The control unit can be a personal computer that runs one or more programs to ensure coordinated operation of all of the components of the system 100. The device 300 and other suitable devices described in greater detail in U.S. Ser. No. 10/426,910, which is hereby incorporated by reference in its entirety.

As previously mentioned, one exemplary rotary device 130 is a multiple station cam-indexing dial that is adapted to perform material handling operations. The dial 130 has an upper surface 132 and means 134 for securely holding one syringe 10 in a releasable manner and in a spaced relationship. Exemplary means 134 is disclosed in U.S. Pat. No. 6,915,823, which is incorporated herein by reference in its entirety.

A post 161 is provided for holding the tip cap 40 after its removal to permit the chamber to be filled with medication. The post 161 can also be formed on the upper surface 132 of the dial 130. Thus, the precise location of the post 161 can vary so long as the post 161 is located where the tip cap 40 can sit without interfering with the operation of any of the automated devices and also the post 161 should not be unnecessarily too far away from the held syringe 10 since it is desired for the automated devices to travel a minimum distance during their operation to improve the overall efficiency of the system 100. The specific shape of the post 161 can likewise vary so long as the post 161 can hold the tip cap 40 so that it remains on the post 161 during the rotation of the dial 130 as the associated syringe 10 is advanced from one station to another station.

While in one exemplary embodiment, the syringes 10 are fed to the rotary device 130 as part of a syringe bandolier (i.e., multiple syringes 10 are disposed in series and interconnected by a web), it will be appreciated that the syringes 10 can be fed to the rotary device 130 in any number of other ways. For example, the syringes 10 can be fed individually into and held individually on the rotary device 130 from a loose supply of syringes 10.

The automated device 300 is a robotic device and preferably, the automated device 300 is a linear actuator with a gripper. For example, the device 300 has first and second positionable gripping arms which are adjustable in at least one direction and which are coupled to and extend downwardly from a block member. For example, each of the gripping arms is movable at least in a direction along the y axis which provide the flexibility and motion control that is desirable in the present system 100. The gripping arms are programmed to work together in tandem so that both arms are driven to the same location and the same time. This permits an object, such as the cap 40, to be held and moved to a target holding location.

The precise movements of the gripper device 300 are described in the '910 application. In general, the gripper device 300 can be any robotic device that can hold and move an object, such as the tip cap 40, from one location to another location.

Figure 19:
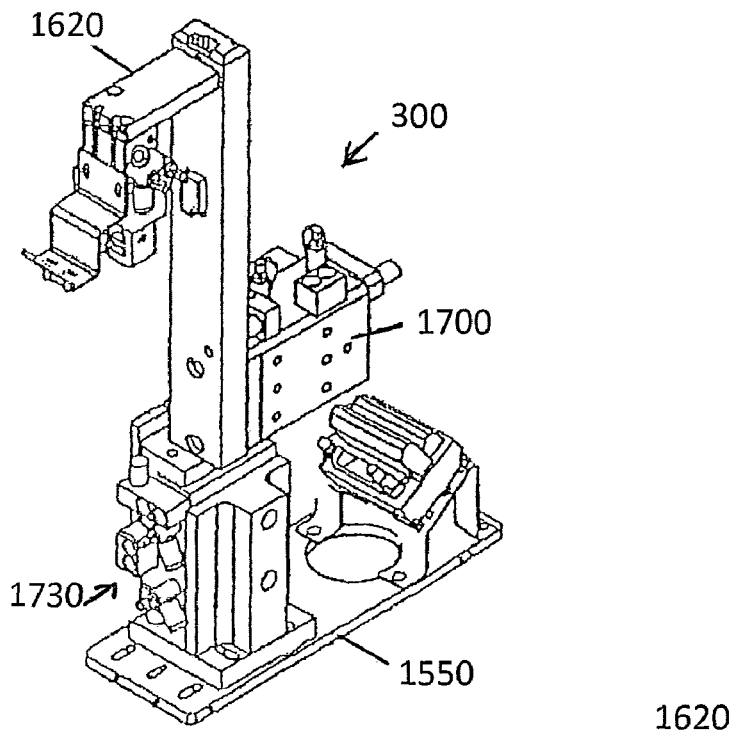
FIG. 19 is a front perspective view of an automated device of FIG. 3 for removing, parking and replacing a tip cap of a syringe.
Figure 21:
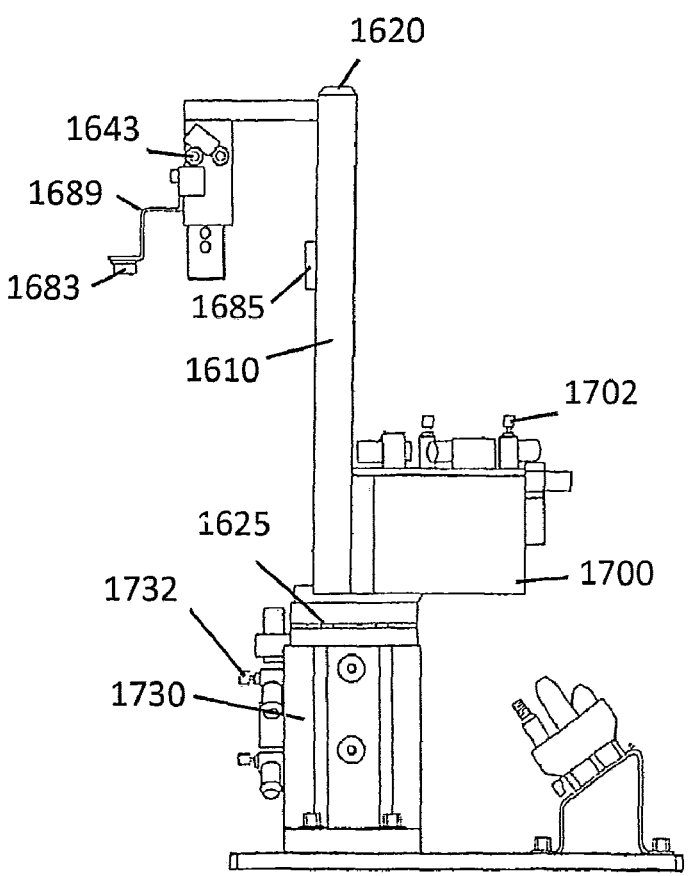
FIG. 21 is a side elevation view of the automated device of FIG. 19.
Figure 20:
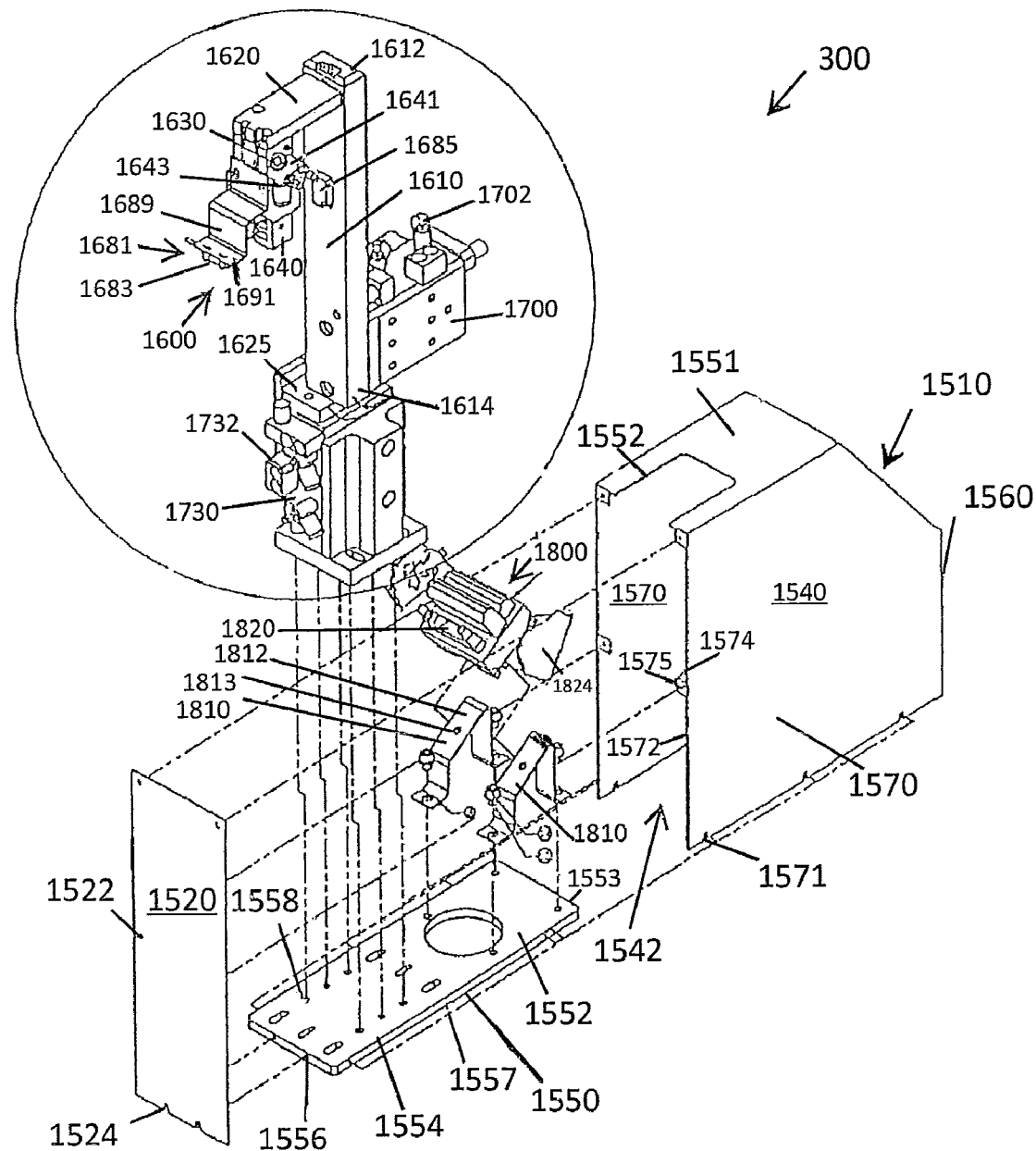
FIG. 20 is an exploded perspective view of the automated device of FIG. 19.

For example, FIG. 19 is a front perspective view of the device 300 and FIG. 20 is an exploded perspective view of the device 300. The exemplary device 300 is formed of a number of working parts that are operatively connected to one another and are also in communication with a controller that is preferably a programmable unit, such as a personal computer or the like, which controls operation of the device 300 as well as other working components. As best shown in the exploded view of FIG. 20, the device 300 includes a housing 1510 and a tip cap gripper unit 1600 that engages the tip cap 40 (FIG. 1) and removes it from syringe 10 and then securely places or parks it on the dial 130 before later retrieving the removed tip cap 40 from the dial 130 and then replacing the tip cap 40 on the syringe 10 using a second tip cap gripper unit 1600 which is part of another device which is described in detail hereinafter. The gripper unit 1600 is partially contained within the housing 1510 except for the adjustable gripper parts that lie outside of the housing 1510 so that they can engage and remove the tip cap 40 of one syringe 10 as it is advanced along the dial 130.

The exemplary housing 1510 includes a front cover plate 1520, a back cover 1540 and a base plate 1550. The front cover plate 1520 is a generally rectangular plate that has a number of openings 1522 formed therein to receive fasteners (not shown) which securely couple the front cover plate 1520 to the back cover 1540. The front cover plate 1520 can also include one or more slots 1524 that also receive fasteners for securely coupling the front cover plate 1520 to the back cover 1540. For example, the slots 1524 can be formed at one edge (e.g., the bottom edge) of the front cover plate 1520.

The back cover 1540 has a substantially open front face 1542 and is formed of a top wall 1551, a rear wall 1560 and a pair of opposing side walls 1570. The top wall 1551 has a cut-out 1552 formed therein to accommodate movement of the gripper unit 1600 within the housing 1510. The top wall 1551 is generally square or rectangular shaped and extends between the side walls 1570 and the rear wall 1560. The opposing side walls 1570 are mirror images of one another and are disposed parallel to and spaced apart from one another. A front edge 1572 of each side wall 1570 includes a number of fastening tabs 1574 that provide mounting surfaces for securely attaching the front cover plate 1520 to the back cover 1540. Two of the fastening tabs 1574 are located at the intersection between the top wall 1551 and the side walls 1570 and two additional fastening tabs 1574 are located below the two tabs 1574 at the top wall 1551. The illustrated tabs 1574 are generally square shaped and are disposed perpendicular to a plane that contains the respective side wall 1570. Openings 1575 are formed in the fastening tabs 1574 for receiving the fasteners and are axially aligned with openings 1522 of the front cover plate 1520. The side walls 1570 also include fastening slots 1571 that receive fasteners for securely attaching the side walls 1570 to the base plate 1550.

The base plate 1550 is securely attached to the side walls 1570 and the front cover plate 1520. The base plate 1550 has a shape and is dimensioned in a complementary manner relative to the other parts of the housing 1510. The illustrated base plate 1550 is generally rectangular shaped and is formed of a body 1552 that includes end edges 1553 and side edges 1554. The end edges 1553 have openings 1556 formed therein to receive fasteners for coupling the front cover plate 1520 to the base plate 1550. Similarly, the side edges 1554 have openings 1557 that receive fasteners for securely coupling the side walls 1570 to the base plate 1550. The body 1552 also includes openings 1558 formed therein for securely mounting various components to the base plate 1550. For example, the gripper unit 1600 is securely attached to the base plate 1550 using fasteners that extend through a number of these openings 1558.

Any number of different types of materials can be used for the housing 1510 and the shape thereof is also likely influenced by design considerations, such as the amount of available space near the dial 130. Thus, the illustrated housing 1510 is merely exemplary in nature and not limiting of the present housing 1510. For example, the housing 1510 can be formed of sheet metal, etc.

The gripper unit 1600 is an assembled unit disposed at the station that is configured to remove the tip cap 40 from the barrel tip 28 of the syringe 10 and place it or park it on the post 161 (FIG. 3). The automated gripper unit 1600 is a robotic device or an automated mechanical device and preferably, one exemplary automated gripper unit 1600 is a pneumatically operated device; however, the gripper unit 1600 can be driven by a motor, etc. The automated gripper unit 1600 includes a vertical base 1610 which is adjustable in at least several directions. For example, the vertical base 1610 has an independent reach (y axis) and vertical axis (x axis) which provides part of the flexibility and motion control that is desirable for the unit 1600. The vertical base 1610 has an upper end 1612 and an opposing lower end 1614 which is operatively coupled to other movable components, as will be described hereinafter, to permit the vertical base 1610 to move in an up/down direction along the x axis and in lateral directions along the y axis. The upper end 1612 is connected to a horizontal support member 1620 (e.g., a top bracket) that extends outwardly away from the vertical base 1610. In one exemplary embodiment, the lower end 1614 is securely attached to a support member 1625.

A block member 1630 is connected to the horizontal support member 1620 and more specifically, the block member 1630 is disposed on an underside of the horizontal support member 1620 so that it is spaced away from the vertical base 1610. The exemplary block member 1630 has a block-like shape and is connected to the underside of the horizontal support member 1620 by one or more connectors, etc.

The gripper unit 400 has first and second positionable gripper arms 1640 which are adjustable in at least one direction and which are coupled to and extend downwardly from the block member 1630. For example, each of the gripper arms 1640 is movable at least in a direction along the y axis to provide the flexibility and motion control that is desirable in the present system 100. The gripper arms 1640 are programmed to work together in tandem so that both arms 1640 are driven alike (e.g., either toward each other or away from one another) and at the same time.

The block member 1630 can house some of the electronic or pneumatic components and the like that permit the gripper arms 1640 to move between the open and closed positions. The coupling between the block member 1630 and the gripper arms 1640 is such that the gripper arms 1640 have the necessary degree of movement to permit the opening and closing thereof.

Each of the gripper arms 1640 (FIG. 3) is a generally inverted F-shaped member that is formed of a vertical section 1642 and a horizontal gripping section 1644 that extends outwardly from one end of the vertical section 1642. The gripping section 1644 has a cut-out or notch 1660 (FIG. 3) formed therein for receiving and gripping a section of the barrel 20 of the syringe 10. Accordingly, the notch 1660 has a complementary shape as the shape of the barrel 20. By being movable along at least the y axis, the gripper arms 1640 can be positioned between an open position in which the opposing gripping sections of the arms 1640 are spaced apart from one another a sufficient distance to permit the tip cap 40 to be received therebetween. In the present invention, the exemplary notch 1660 has a "V" shape so that it has sufficient surface area to securely hold the tip cap 40 when the gripping section 1644, but not so much that disengaging from tip cap 40 interferes with placement on pin 161 or syringe tip 28. It will be appreciated that the notch 1660 can be arcuate in shape as well as being shaped as a serated V, serated semi-circle or a smooth V. Each arm also includes a pair of posts 1661 that extend outwardly from the vertical wall 1642 toward the open notch 1660. The exemplary posts 1661 are generally rectangular or square in cross section and they do not extend fully across the width of the gripping section 1644. In other words, the post 1661 preferably does not extend beyond the leading edge of the gripping section 1644. When the tip cap 40 is gripped by the arms 1640, the tip cap 40 is disposed between the posts 1661 and the gripping sections 1644 and more specifically, the tip cap 40 fits between the bottom face of the posts 1661 and the upper face of the gripping sections 1644. The posts 1661 serve to locate the tip cap 40 and make sure that the tip cap 40 remains in the desired gripping position as it is moved from one location to another.

In the closed position, the gripping sections 1644 of the arms 1640 are brought together so that they either seat against one another or are in very close proximity to one another. When the gripping sections 1644 come together in the closed position, the notches 1660 define an opening that permits the tip cap 40 to nest within the gripping sections 444.

One knowledgeable in the state of the art will recognize that several motion control devices (i.e., motors, hydraulic drives, pneumatics, etc.) can be used to conduct the linear motion required of the various stations. In the immediate invention, different motion control devices are used for their defined operation. For stations 150 and 180, the motion control devices are powered by pneumatic pressure. Stations 150 and 180 each have three pneumatic motion control devices. For each of these motion control devices, there is a constant pneumatic pressure forcing the certain component to its safe "home" position and a single stage valve that is activated by input from the system controller 1670 that over pressurizes the pneumatic cylinder so that the mechanical component can advance to the endstop opposite to its home position.

In the open position of the gripper arms 1640, they are spaced sufficiently from one another so as to permit the tip cap 40 to be freely disposed between the gripping sections 444. On an input signal from the control unit 1670 (e.g., a programmable actuator, microprocessor, etc.), the gripper arms 1640 are driven to the first position. The control unit 1670 instructs the gripper unit 400 to perform various operations for removing the tip cap 40 from the barrel tip 28, parking the tip cap 40 on the post 161 and then, using a second controller mechanism, replacing the tip cap 40 on the filled syringe 10. When such an operation is performed, the vertical base 1610 is driven in a number of different directions until proper alignment is realized. In other words, the tip cap 40 is disposed between the gripping sections 1644 of the opposing arms 1640 and more specifically, the gripping sections 1644 are disposed adjacent the base section 41 of the tip cap 40 underneath the flange 43 with the notches being aligned with the outer surface of the base section 41. An actuator or the like of the device 1600 is then deactivated causing the gripper arms 1640 to move inwardly toward one another until the gripping sections 1644 seat against the outer surface of the base section 41 of the tip cap 40. In this closed position, the gripper arms 1640 apply a force against the base section 41 so that the tip cap 40 is securely held by the gripping sections. When the gripper arms 1640 are driven to the closed position, the gripping sections seat against one another and the notches align such that the gripping sections substantially encircle the base section 41.

Since the gripper unit 1600 is preferably a pneumatic device, a number of pneumatic controls are disposed near the gripper arms 440. More specifically, the gripper arms 1640 are pneumatic devices and therefore, a first pneumatic control 1641 is connected to the block member 1630. The first pneumatic control 1641 is integral to block member 1630 and includes first and second flow control valves 1643 that are of a point locked type, with the positions set at the time of manufacture. For example, the valves 1643 have adjustable knobs that permit a certified field service engineer or technician to adjust the pneumatic pressure that is present at the gripper arms 1640 to assist in the opening and closing of the gripper arms 1640. As will be appreciated, the unit 1600 can be a pneumatically based system since the operation of the vertical base 1610 only requires the vertical base 1610 to be driven between two fixed positions in one direction of movement.

The gripper unit 1600 (FIG. 20) also preferably includes a sensor assembly, generally indicated at 1681, for sensing whether a tip cap 40 is present between the gripper arms 1640. One exemplary sensor assembly 481 includes a sensor device 1683 and a reflector 1685 that is spaced therefrom. The sensor device 1683 is formed of one or more sensors that are securely attached to a support bracket 1689 that is attached to the block member 1630. The support bracket 1689 has two sections that each has an L-shape and therefore the bracket 1689 resembles a series of steps. A bottommost section 1691 of the support bracket 1689 is the section that holds the one or more sensors 1683. The support bracket 1689 is disposed so that the gripper arms 1640 lie between the support bracket 1689 and the vertical base 1610.

According to one exemplary embodiment, the sensors 1683 are LED type sensors or the like which emit a light beam in a predetermined direction. There are preferably two LED sensors 1683 that emit light beams in a direction toward the gripper arms 1640 and more specifically, the light beams are targeted between the gripper arms 1640 where the tip cap 40 is to be located when the gripper arms 1640 properly grip and retain the tip cap 40.

The reflector 1685 is securely attached to the vertical base 1610 and is axially aligned with the sensors 1683 so that when the sensors 1683 are actuated, the light beams are emitted from the sensors 1683 and, if no obstruction is present, the light beams pass across the space between the support bracket 1689 and the inner face of the rear cover 1540. If a tip cap 40 is present between the gripper arms 1640, then the light beams of the sensors 1683 will be impinged or otherwise broken since the tip cap 40 lies within the path of the light beam when it is securely held between the gripper arms 1640. When the tip cap 40 is present, the light beams of the sensors 1683 do not make contact with the reflector and therefore, the light beams are not reflected back to the sensors 1683. Because the sensors 1683 are in communication with the control unit 1670, a break in the light beam generates a control signal that is delivered to the control unit 1670 to indicate that an object, such as the tip cap 40, is present between the gripper arms 1640. Conversely, if the gripper arms 1640 are instructed to remove the tip cap 40, they are actuated and moved to a position for gripping and retaining the tip cap 40 and if for some reason, the tip cap 40 is not removed properly, then the sensor's light beam is not impinged by the tip cap 40. The light beam of the sensors 1683 pass completely to the reflector 1685 since there is no tip cap 40 present between the gripper arms 1640. The control unit 1670 therefore does not receive the control signal indicating the presence of one tip cap 40 between the gripper arms 1640. After a predetermined time period, the control unit 1670 will reject the syringe 10 if the presence of the tip cap 40 is not detected. Once the syringe 10 is rejected, the dial 130 is advanced and the tip cap process is started over with the next adjacent syringe 10 on the dial 130 being advanced so that it is in position for the gripper unit 1600 to act and remove the tip cap 40. If the sensor device 1683 detects the presence of a tip cap 40 at a time when the presence is expected, the control signal from the sensor device 1683 is received by the control unit 1670 and the gripper unit 1600 is instructed to continue its process of removing, parking, or replacing the tip cap 40.

The gripper unit 1600 includes a number of pneumatic control devices and more specifically, the gripper unit 1600 includes a second pneumatic control device 1700 and a third pneumatic control device 1730. The second pneumatic control device 1700 controls movement of the vertical base 1710 in towards and out away from the dial 130. In other words, the second pneumatic control device 1700 moves the vertical base 1710, as well as the gripper arms 1740, in a direction toward the dial 130 and in a direction away from the dial 130. The second pneumatic control device 1700 is similar to the previously described motion control device 1631 with its "home" position being out, away from the dial 130.

Figure 4:
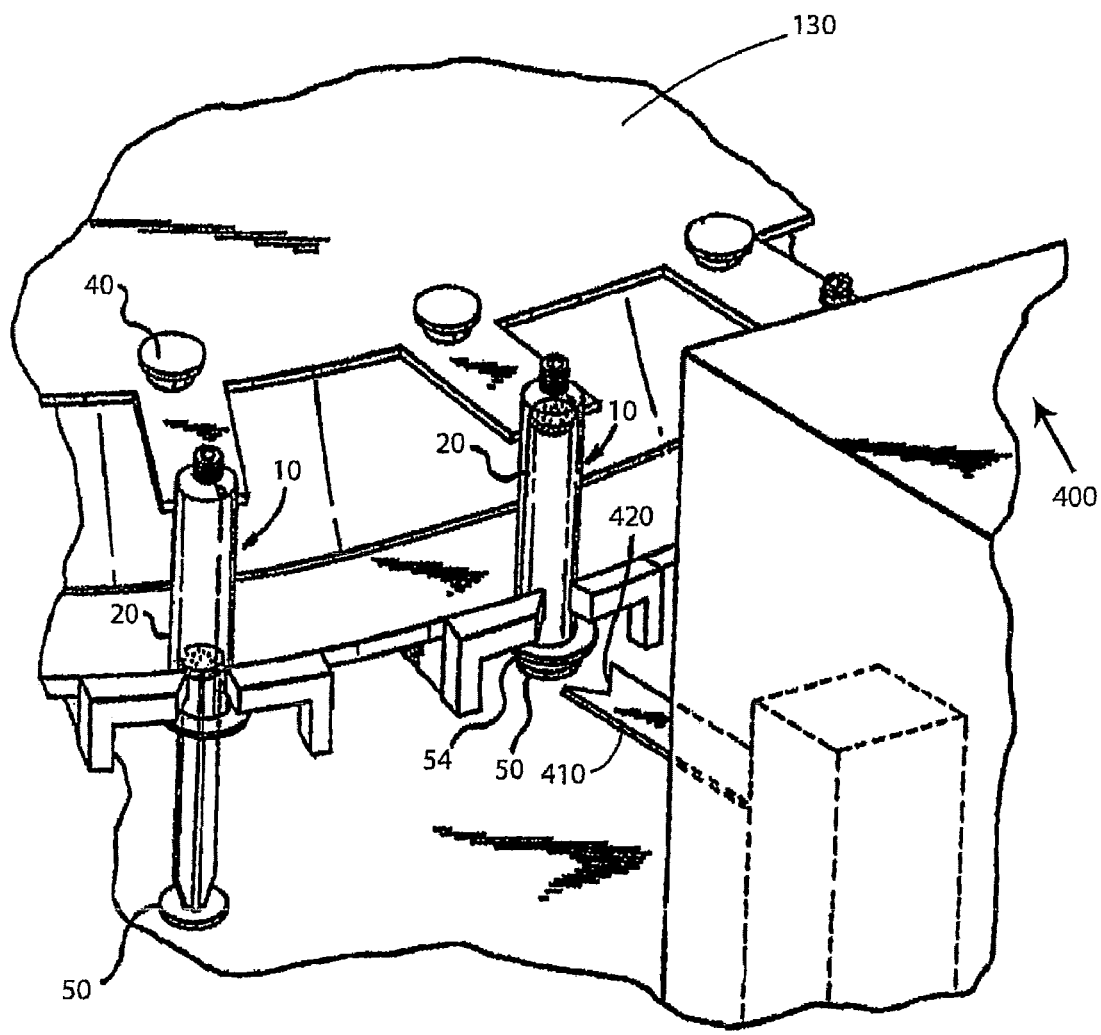
FIG. 4 is a local perspective view of a device for extending a plunger of the syringe.

In the illustrated embodiment, the second pneumatic control device 1700 is disposed at a lower end of the vertical base 1610 and preferably is operatively coupled thereto so that actuation of the control device 1700 causes the selective, controlled movement of the vertical base 1610 in and out from the dial 130. As shown in FIG. 4, both the lower end of the vertical base 1610 and the second pneumatic control device 1700 are disposed on a support surface 1711 of the support member 1625. More specifically, the support member 1625 has one or more guide tracks 1713 formed therein to permit the controlled in and out movement of the vertical base 1610. As the vertical base 1610 moves in the in and out directions, it moves from one end of the support member 1625 to the other end of the support member 1625 in a controlled manner so that the gripper arms 1640 are moved from an out position, where the gripper arms 1640 are disposed away from the dial 130, to an in position, where the gripper arms 1640 are disposed above the dial 130 as represented by the syringe 10 in FIG. 3. In this embodiment where pneumatic controls are used, the vertical base 1610 travels a fixed distance, namely the distance between the out position and the in position and vice versa.

The second pneumatic control device 1700 includes a number of adjustable control features that permit a certified field service engineer or technician to vary the operating parameters of the device 1700. For example, the second pneumatic control device 1700 can include one or more control valves 1702 for controlling and adjusting the pneumatic pressure within the second pneumatic control device 1700. In the illustrated embodiment, these control valves 1702 are in the form of control knobs that can be easily adjusted by an appropriately certified field service engineer or technician.

The third pneumatic control device 1730 controls movement of the vertical base 1610 in the up-down directions. In other words, the third pneumatic control device 1730 moves the vertical base 1610, as well as the gripper arms 1640, and the second pneumatic control device 1700, in a vertical direction. The third pneumatic control device 1730 is similar to the previously described motion control device 1631 with its "home" position being up, keeping the gripper mechanism 1640 away from the dial 130.

In the illustrated embodiment, the third pneumatic control device 1730 is disposed below the support member 1725 and therefore is generally below the lower end of the vertical base 1710. Preferably, the third pneumatic control device 1730 is operatively coupled to the support member 1725 so that actuation of the third pneumatic control device 1730 causes the selective, controlled movement of the vertical base 1610 in up-down directions. As previously specified, one knowledgeable in the state of the art recognizes that controlling the vertical motion of certain components connected to the support member 1725 can be accomplished by one of a number of motion controllers (i.e., motors, hydraulic drives, pneumatics, etc.) In the present invention, the up-down movement of the vertical base 1610 is caused by a pneumatic cylinder or other moving parts that are pneumatically driven.

As the vertical base 1610 moves in the up and down directions, the vertical base 1610 is raised and lowered relative to the housing 1610 in a controlled manner so that the gripper arms 1640 are moved from a raised position, where the gripper arms 1640 are disposed a maximum distance away from the upper surface of the dial 130, to a lowered position, where the gripper arms 1640 are disposed a minimum distance from the upper surface of the dial 130. This lowered position allows for interaction with the tip cap 40 and either the syringe tip 28 or pin 161. In this embodiment where pneumatic controls are used, the vertical base 1610 travels a fixed distance, namely the distance between the raised position and the lowered position and vice versa.

The third pneumatic control device 1730 includes a number of adjustable control features that permit a trained and certified field service engineer or technician to vary the operating parameters of the device 1730. For example, the third pneumatic control device 1730 can include one or more control valves 1732 for controlling and adjusting the pneumatic pressure within the third pneumatic control device 1730. In the illustrated embodiment, these control valves 1732 are in the form of control knobs that can be easily adjusted by the certified field service engineer or technician.

The unit 1600 (FIG. 4) also includes a connector module 1800 that is disposed within the housing 1510 and is securely attached to the base plate 1550 using a pair of angled mounting brackets 1810. The angled mounting brackets 1810 are spaced apart from one another and are mounted to the base plate 1550 using fasteners 1552 or the like. Each bracket 1810 includes a planar surface 1812 that has an opening 1813 formed therethrough to receive a fastener for mounting a module 1820 to the clamps 1810. The module 1820 is the input/output connector block for the entire station. At each end of the module 1820, an end stop 1824 is provided for limiting the movement of module 1820. More specifically, the end stops 1824 keep the input/output blocks of the module 1820 from sliding off the railed tray to which the module 1820 is mounted. The connector module 1810 is located adjacent the unit 1600 and more specifically, it is located behind the third pneumatic control device 1730 (e.g., closer to the rear wall 1560). The connector module 1710 is thus disposed between the unit 1600 and the rear wall 1560.

The operation of the gripper unit 1600 is now described in detail. To remove a tip cap 40, the third pneumatic control device 1730 is deactivated (valves are closed) so that the vertical base 1610 and the gripper arms 1640 are in the raised position. At the same time, the second pneumatic control device 1700 is not actuated (valve closed) and therefore, the vertical base 1610 is in the out position. For ease of description, this orientation is referred to as a starting position which permits the dial 130 to be advanced so that one syringe 10 is delivered to a position where the syringe 10 is in axial alignment with the gripper arms 1640. The gripper arms 1640 are in a closed position in the starting position. In other words, the first pneumatic control 1641 is in an deactivated position, thereby causing the two gripper arms 1640 to be closed. When the syringe 10 is advanced to a position where the gripper arms 1640 are axially aligned with the syringe 10, the syringe 10 likewise is in a start position.

To initiate the tip cap removal cycle, the pneumatic control device 1641 is activated so that the gripper arms 1640 are opened. The third pneumatic control device 1730 is then activated so that the pressure in the valves 1732 is released, thereby causing the device 1730 to assume the lowered position. In this lowered position, the tip cap 40 of the syringe 10 is disposed between the gripper arms 1640 and then the first pneumatic control 1641 is deactivated so that the gripper arms 1640 are closed and the tip cap 40 is nested within the gripper arms 1640. Because of the complementary shape of the gripper arms 1640, the tip cap 40 is securely held therebetween and is ready to be removed from the syringe 10.

To remove the tip cap 40 from the syringe 10, the third pneumatic control device 1730 is deactivated so that it moves to the raised position. Because the first pneumatic control 1641 remains deactivated, the gripper arms 1640 remain in engagement with the tip cap 40 as the third pneumatic control device 1730 assumes the raised position and this movement in a direction away from the syringe 10 causes the tip cap 40 to be lifted off of the syringe 10 as it is held between the gripper arms 1640. It will be appreciated that the sensor device 1683 is preferably used to sense whether the tip cap 40 is securely being held by the gripper arms 1640. More specifically, the light beam of the sensor 1683 is broken when the tip cap 40 comes between the sensor 1683 and the reflector 1685 and this signals to the controller 1670 that an object, e.g., the tip cap 40, is present between the closed gripper arms 1640. If the sensor 1683 does not detect the presence of a tip cap 40 when the gripper arms 1640 are closed in this position, then the controller 1670 will cause the vertical base 1610 to return to the start position and the removal and parking operations are started again.

Once the third pneumatic control device 1730 reaches the raised position, the second pneumatic control 1800 is then actuated and this causes the vertical base 1610 to go from the out position to the in position. In the in position, the gripper arms 1640 holding the tip cap 40 are disposed immediately above the pin (post) 161 for parking of the tip cap thereon. In other words, movement of the vertical base 1610 from the out position to the in position causes the gripper arms 1640 to move from a position over the syringe 10 to a position over the pin 161. The tip cap 40 is now ready for parking on the pin 161.

To park or place the tip cap 40 on the pin 161, the third pneumatic control device 1730 is activated (valve is open) so that the third pneumatic control device 1730 moves back to the lowered position. In the lowered position, the gripper arms 1640 are immediately above the pin 161. The tip cap 40 is also axially aligned on the pin 161 so that release of the tip cap 40 results in the tip cap 40 being held by the pin 161. To release the tip cap 40, the first pneumatic control 1641 is activated (the valve is opened) so that the gripper arms 1640 move from the closed position to the open position. As the gripper arms 1640 move apart from one another, the tip cap 40 is released from the grip thereof.

Once the tip cap 40 is securely retained on the pin 161, the third pneumatic control device 1730 is deactivated so that the vertical base 1610 moves from the lowered position to the raised position where the gripper arms 1640 are a significant distance from the dial 130. In addition to the actuation of the third pneumatic control device 1730, the second pneumatic control device 1800 is deactuated resulting in the vertical base 1610 moving from the in position to the out position. This movement facilitates the further advancement of the dial 130 and the syringe 10 since the gripper arms 1640 are moved away from the dial 130 so as to not obscure access thereto. It will be appreciated that the vertical base 1610 has now reassumed the starting position and the process can be repeated by advancing the dial 130 so that another syringe 10 is brought into place and the various components of the gripper unit 1600 are then controlled and moved in the manner just previously described for gripping, removing, and parking the tip cap 40 on the pin 161.

As previously mentioned, the sixth station 180 also includes a device 300 for replacing the tip cap 40 on the syringe 10 after the syringe 10 is filled with the medication, etc. at an earlier station, e.g., third station 170. The device 300 that is used at the third station 150 for removing and parking the tip cap 40 from the syringe 10 prior to the syringe being filled is preferably the same type of device as the device 300 that is used at sixth station 180 for retrieving the tip cap 40 from the pin 161 and then replacing it on the syringe 10. The steps of operation are slightly different at the sixth station 180 since the tip cap 40 is initially retained on the pin 161 and not the syringe 10 at this station.

In the starting position at the sixth station 180, the second pneumatic control device 1800 is activated, while the first pneumatic control device 1641 and the third pneumatic control device 1730 are both deactivated (valves are closed) so that the vertical base 1610 is in the raised position as well as being in the in position. Thus, the gripper arms 1640 are generally above the pin 161 since the vertical base 1610 is in the in position. The first pneumatic control 1641 is preferably in the closed position so that the gripper arms 1640 are closed with respect to one another. The first pneumatic control device 1641 is activated and the third pneumatic control device 1730 is then activated so that the gripper arms 1640 open and the vertical base 1610 goes from the raised position to the lowered position. In the lowered position, the gripper arms 1640 surround the tip cap 40 that is resting on the pin 161. Next, the first pneumatic control 1641 is deactivated resulting in the gripper arms 1640 closing and securely capturing and retaining the tip cap 40. In other words, the tip cap 40 nests within the gripper arms 1640 and is ready to be removed and lifted from the pin 161. At this point in time, the sensor device 1683 is preferably used to determine whether the tip cap 40 is present between the gripper arms 1640. If the tip cap 40 is present and is captured between the gripper arms 1640, then the light beam of the sensor 1683 is broken and a signal is delivered to the controller 1670. The controller 1670 will then instruct the gripper unit 1600 to continue the tip cap replacement operation. If the sensor device 1683 does not detect that the tip cap 40 is present between the gripper arms 1640, the gripper arms 1640 can be instructed to attempt the grasping process again or the controller 1670 can be instructed to restart the entire operation by returning the vertical base 1610 to the starting position and then the dial 130 is advanced and then process is started over again to attempt to grasp and capture the tip cap 40 from the pin 161 so that it can be replaced onto a filled syringe 10.

To lift the tip cap 40 from the pin 161, the third pneumatic control device 1730 is deactivated resulting in the vertical base 1610 moving from the lowered position to the raised position. As the vertical base 1610 is raised, the tip cap 40 is removed and lifted from the pin 161 since the tip cap 40 is securely held by the gripper arms 1640. The vertical base 1610 is moved to the raised position and then the second pneumatic control device 1800 is activated causing the vertical base 1610 to move from the in position to the out position. Thus, the vertical base 1610 and the gripper arms 1640 thereof are moved away from the dial 130 and the gripper arms 1640 are moved from a position where they are disposed over the pin 161 to a position where they are disposed over the uncapped syringe 10. The uncapped syringe 10 has been previously filled with medication and therefore is ready to be capped.

To cap the syringe 10, the third pneumatic control device 1730 is activated to cause the vertical base 1610 to move from the raised position to the lowered position. When the vertical base 1610 moves to the lowered position, the tip cap 40 is press fitted onto the barrel tip 28 of the uncapped syringe 10; however, the tip cap 40 is still securely held between the gripper arms 1640. The first pneumatic control 1641 is then activated to cause the gripper arms 1640 to move from the closed position to the open position. When the gripper arms 1640 open, the tip cap 40 is free from the gripper unit 1600 and remains fixedly attached to the barrel tip 28 of the syringe 10. The vertical base 1610 is then moved to the raised position by deactivating the third pneumatic control device 1730 so that the gripper arms 1640 are removed from the syringe 10 and are delivered to a position where the gripper arms 1640 are disposed above and spaced from the barrel tip 28 of the syringe 10. To start the replacing operation again, the vertical base 1610 is returned to the starting position by deactivating the second pneumatic control device 1800 to cause the gripper arms 1640 to move to the in position so that they are disposed above the dial 130 and more specifically, above the path that the pin 161 follows as the dial 130 advances. The dial 130 is then advanced until a new tip cap 40 is disposed underneath the gripper arms 1640 and then the process is started over.

The capped syringe 10 can then be transferred to other stations, such as a station where the syringe in bandolier form is cut into individual syringes 10 that are labeled for particular patients. The syringes 10 can then be unloaded from the dial 130 by a suitable mechanical device. The syringe 10 is then further processed as for example by being delivered to a storage receptacle where it is stored or by being delivered to a transporting device for delivery to the patient.

Now referring to FIG. 4, the system 100 also includes a device 400 for extending the plunger 50 of one uncapped syringe 10 after it has had its tip cap 40 removed therefrom.

For ease of illustration, the device 400, as well as the device 300, are described as being part of the third station 150 of the system 100. The device 400 extends the plunger 50 so that the syringe 10 can receive a desired dose based upon the particular syringe 10 being used and the type of application (e.g., patient's needs) that the syringe 10 is to be used for. The device 400 can have any number of configurations so long as it contains a feature that is designed to make contact with and withdraw the plunger 50. In one exemplary embodiment, the automated device 400 is a robotic device and preferably, the automated device 400 is a linear actuator with a gripper. For example, one exemplary device 400 is a mechanical device that has a movable gripper 410 that includes a gripping edge 420 that engages the flange 54 of the plunger 50, as shown in FIG. 4, and then the gripper 410 is moved in a downward direction causing the plunger 50 to be moved a predetermined amount. For example, the gripper 410 can be the part of an extendable/retractable arm that includes the gripping edge 420 for engaging the syringe 10 above the plunger flange 54. When an actuator or the like (e.g., stepper motor) causes the gripper 410 to move in a downward direction, the gripping edge 420 seats against the flange 54 and further movement of the gripper 410 causes the extension of the plunger 50. Once the plunger 50 has been extended the prescribed precise distance, the gripper 410 moves laterally away from the plunger 50 so that the interference between the flange 54 of the plunger 50 and the gripping edge 420 no longer exits. In other words, the gripper 410 is free of engagement with the plunger 50 and can therefore be positioned back into its initial position by being moved laterally and/or in an up/down direction (e.g., the gripper 410 can move upward to its initial position). An exemplary plunger extending device is described in commonly assigned U.S. patent application Ser. No. 10/457,066, which is hereby incorporated by reference in its entirety.

Thus, the device 400 complements the device 300 in getting the syringe 10 ready for the fluid transfer station at which time, a prescribed amount of medication or other medication is dispensed into the chamber 30 of the barrel 20 as will be described in greater detail hereinafter.

Of course, it will be appreciated that the syringes 10 can be provided without caps 40 and thus, the device 300 is not needed to remove caps 40 if the syringes 10 are loaded onto dial 130 without caps 40.

The device 400 is part of the overall programmable system and therefore, the distance that the gripper 410 moves corresponds to a prescribed movement of the plunger 50 and a corresponding increase in the available volume of the chamber of the barrel 20. For example, if the prescribed unit dose for a particular syringe 10 is 8 ml, then the controller instructs the device 400 to move the gripper 410 a predetermined distance that corresponds with the plunger 50 moving the necessary distance so that the volume of the barrel chamber is at least 8 ml. This permits the unit dose of 8 ml to be delivered into the barrel chamber. As described below, the device 400 can be operated multiple times with reference to one syringe 10 in that the plunger 50 can be extended a first distance during a first operation of the device 400 and a second distance during a subsequent second operation of the device 400.

In one example, after the syringe 10 has been prepared by removing the tip cap 40 and extending the plunger 50 a prescribed distance, the syringe 10 is then delivered to the fluid transfer station 170 where a fluid transfer device 500 prepares and delivers the desired amount of medication.

Figure 5:
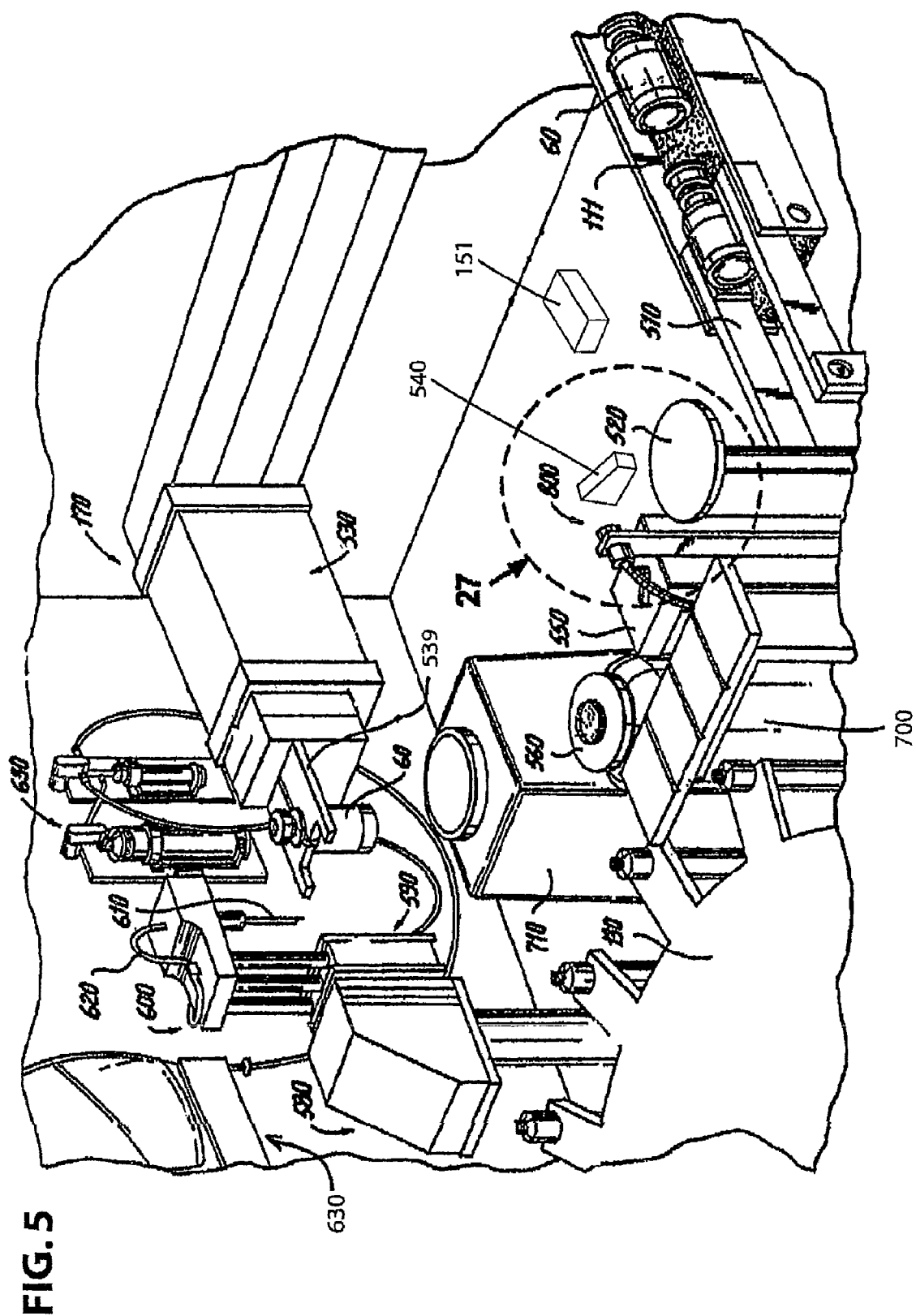
FIG. 5 is a local perspective view of fluid transfer and vial preparation equipment in a fluid transfer area of the automated system.

Now turning to FIG. 5 in which a drug preparation area is illustrated in greater detail to show the individual components thereof. More specifically, a drug transfer area for the vial mode of operation of the system 100 is illustrated and is located proximate the rotary dial 130 so that after one drug vial 60 is prepared (reconstituted), the contents thereof can be easily delivered to one or more syringes 10 that are securely held in nested fashion on the rotary dial 130. As previously mentioned, drug vials 60 are stored typically in the storage cabinet 110 and can be in either liquid form or solid form or even be empty. A driven member, such as a conveyor belt 111, delivers the drug vial 60 from the cabinet 110 to a first robotic device (e.g., a pivotable vial gripper mechanism) 510 that receives the vial 60 in a horizontal position and after gripping the vial with arms (grippers) or the like, the mechanism 510 is operated so that the vial 60 is moved to a vertical position relative to the ground and is held in an upright manner.

The mechanism 510 is designed to deliver the vial 60 to a rotatable pedestal 520 that receives the vial 60 once the grippers of the mechanism 510 are released. The vial 60 sits upright on the pedestal 520 near one edge thereof that faces the mechanism 510 and is then rotated so that the vial 60 is moved toward the other side of the pedestal 520. It will be understood that any number of different robotic mechanisms can be used to handle, move and hold the vial.

As the pedestal rotates, the vial 60 is scanned as by a barcode reader 151 or the like and preferably a photoimage thereof is taken and the vial 60 is identified. If the vial 60 is not the correct vial, then the vial 60 is not used and is discarded using a gripper device that can capture and remove the vial 60 from the pedestal before it is delivered to the next processing station. The central control has a database that stores all the identifying information for the vials 60 and therefore, when a dose is being prepared, the controller knows which vial (by its identifying information) is to be delivered from the cabinet 110 to the pedestal 520. If the scanning process and other safety features does not result in a clear positive identification of the vial as compared to the stored identifying information, then the vial is automatically discarded (e.g., returned to a further inspection station) and the controller will instruct the system to start over and retrieve a new vial.

The reader, such as a scanner, 151 can also read the vial 60 to ensure that the proper vial 60 has been delivered and gripped by the robotic device. This is another safety check and can be implemented with barcodes or the like. The reader 151 initially reads the barcode or other identifying information contained on the vial 60 and this read information is compared to a stored database that contains the inputted drug information. If the product identification information does not match, the operator is notified and the vial 60 is not advanced to the next station.

If the vial 60 is identified as being the correct vial, then a vial gripper device (robotic device) 530 moves over to the pedestal for retrieving the vial 60 (alternatively, this robotic device can be the same robotic device that delivers the vial 60 to the pedestal). The vial gripper device 530 is configured to securely grip and carry the vial in a nested manner to the next stations as the drug is prepared for use. Details and operation of the vial gripper device 530 are described in detail in U.S. patent application Ser. No. 11/434,850, which is hereby incorporated by reference in its entirety. The robotic device 530 includes a pair of grippers or arms 539 (gripper unit) that are positionable between closed and open positions with the vial 60 being captured between the arms in the closed position in such a manner that the vial 60 can be securely moved and even inverted and shaken without concern that the vial 60 will become dislodged and fall from the arms. The arms thus have a complementary shape as the vial 60 so that when the arms close, they engage the vial and nest around a portion (e.g., neck portion) of the vial 60 resulting in the vial 60 being securely captured between the arms. As with some of the other components, the arms can be pneumatically operated arms or some other mechanical devices.

In order to retrieve the vial 60 from the pedestal 520, the device 530 is driven forward and then to one side so that it is position proximate the pedestal 520. The gripper unit 539 is then moved downward so that the arms, in their open position, are spaced apart with the vial 60 being located between the open arms. The gripper unit 539 is then actuated so that the arms close and capture the vial 60 between the arms. Next the robotic device 530 is moved upward and the device 530 is driven back to the opposite side so as to introduce the vial 60 to the next station. The vial 60 is also inverted by inversion of the gripper unit 539 so that the vial 60 is disposed upside down.

The inverted vial 60 is then delivered to a station 550 where the vial 60 is prepared by removing the safety cap from vial 60. This station 550 can therefore be called a vial decapper station. Any number of devices can be used at station 550 to remove the safety cap from the vial. For example, several exemplary decapper devices are disclosed in commonly-assigned U.S. Pat. No. 6,604,903 which is hereby incorporated by reference in its entirety. After the vial 60 is decapped, the vial is then delivered, still in the inverted position, to a cleaning station 560 where the exposed end of the vial is cleaned. For example, underneath the removed vial safety cap, there is a septum that can be pierced to gain access to the contents of the vial. The cleaning station 560 can be in the form of a swab station that has a wick saturated with a cleaning solution, such as an alcohol. The exposed area of the vial 60 is cleaned by making several passes over the saturated wick which contacts and baths the exposed area with cleaning solution. After the vial 60 is cleaned at the station 560, the gripper unit 539 rotates so that the vial 60 is returned to its upright position and remains held between the gripper arms.

Figure 8:
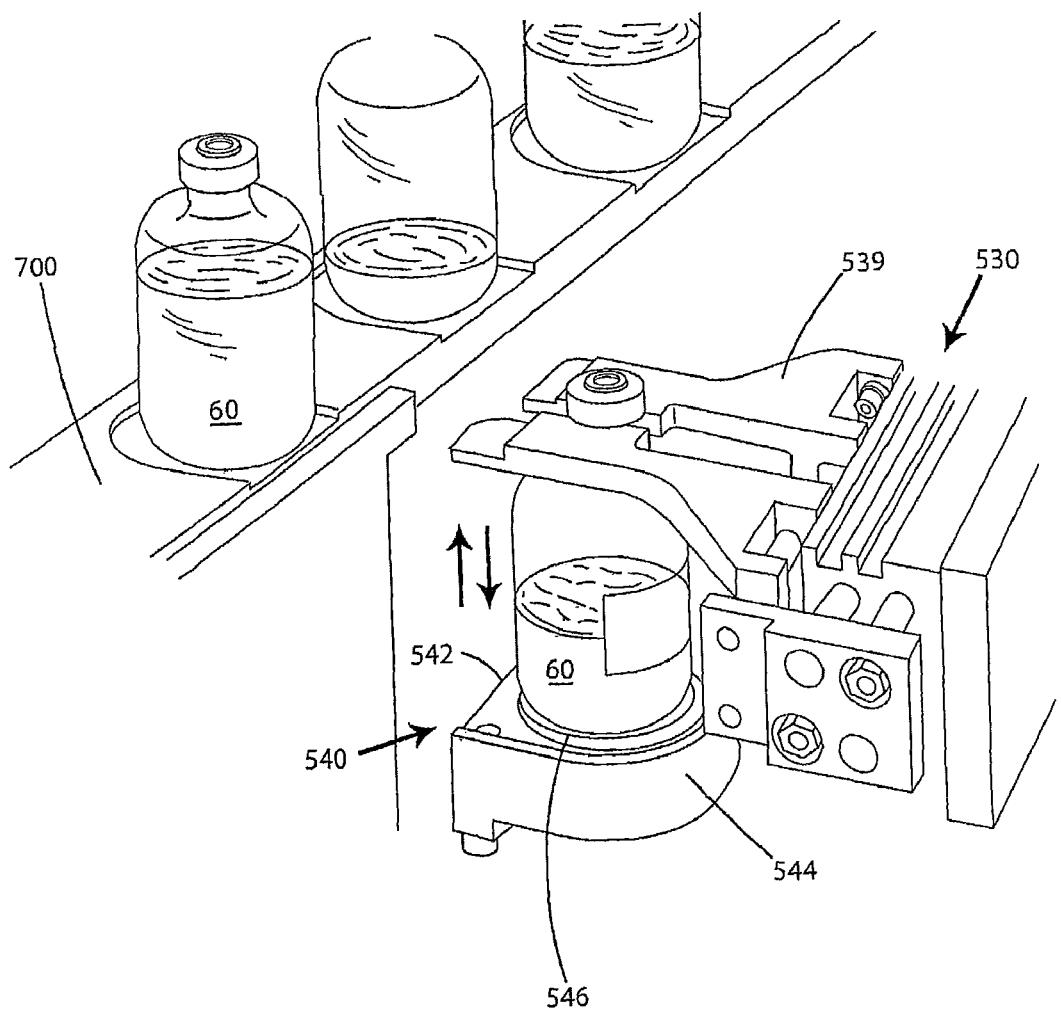
FIG. 8 is a local perspective view of a multi-use vial holding station and a vial weigh station.

The vial 60 can then be delivered to a weigh station 540 (FIG. 8) where the weight of the vial with solid medication (or an empty vial or any other object) is measured and stored in the computer system. Any number of different devices, such as scales, can be used to weigh the vial; however, one exemplary device for weighing the vial 60 and any other object for that matter, is a load cell 542. Load cell 542 is a transducer for the measurement of force or weight, usually based on a strain gauge bridge or vibrating wire sensor. In particular and as shown in FIG. 8, the load cell 542 includes a housing or body 544 that contains the working components and electronics of the load cell 542 and a platform 546 on which the item, in this case, the vial, to be weighed is placed.

The load cell 542 is part of an overall automated and integrated system and therefore, it contains software that communicates with the master controller so that the operation of the complete system 100 can be controlled, including the movement of the robotic device 530 that holds and transport the vial 60 from one location to another location. As shown in FIG. 8, the vial 60 is held by the robotic device about the neck portion and can therefore be delivered onto the load cell platform 546. In one embodiment, the robotic device moves the vial 60 from the pedestal 520 to the platform 546.

The software controlling the robotic device is configured so that the vial grippers of the robotic device are first approximately level with the standby pedestal 520 and at this point, the software of the load cell gathers a predetermined number, such as 10-15 (e.g., 15) weights from the load cell 542 which are considered the tare weight. The vial 60 is then shuttled down to a predetermined distance, such as 2.5 mm, above the load cell platform 546. From this predetermined distance (e.g., 2.5 mm), the load cell software shuttles the vial 60 down towards the load cell platform 546 very slowly, while monitoring the weights returned by the load cell 542 to determine the exact moment the vial makes contact with the platform 546 (i.e., which will register a marked increase in observed weight). At the moment the vial contact the platform, the software instructs the vial grippers to open and all vertical movement of the vial is stopped. A predetermined time, such as 0.5 seconds, after the vial grippers open, the software collects a predetermined number, such as 10-15 (e.g., 15) weight measurements from the load cell, which shall be considered the weight of the vial and the load cell platform.

Figure 17:
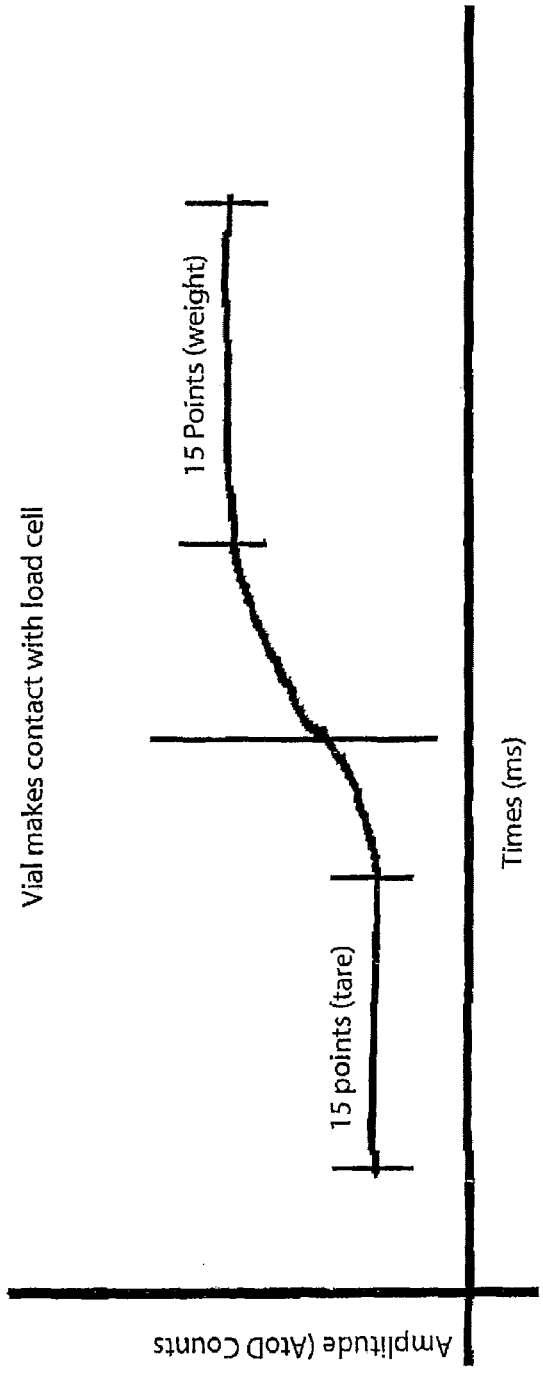
FIG. 17 is a graph of the data obtained by a load cell for determining a weight of the contents of the vial to ensure proper reconstitution of the medication.

The data collected by the load cell can be processed in any number of different ways and in one embodiment, as shown in FIG. 17, a graph is created where the x axis is the measured amplitude (AtoD counts) and the y axis is the time (ms). The point at which the vial makes contact with the load cell 542 is indicated at line 545. The vial weight (AtoD counts) is equal to the measured weight–tare. The vial weight (grams) is equal to (vial weight (AtoD counts)*slope)+intercept. In another embodiment, data is not displayed but is manipulated inside the master controller and the final results are used for system reaction.

As will be described below, since the initial weight of the vial is measured and stored and later, the weight of the reconstituted drug in the vial is calculated, a safety check can be performed to determine if the proper drug product was fabricated.

In another embodiment, such as in a serial dilution scheme, an empty child vial is weighed and diluent is added and weighed. After that, drug is added to the vial with diluent and weighed. Then the system calculates the amount of the diluent and drug added to the vial and knows the final composition of the drug in the vial.

The device 530 then advances forward to the fluid transfer station 170 according to one embodiment. The fluid transfer station 170 is an automated station where the medication (drug) can be processed so that it is in a proper form for delivery (injection) into one of the syringes 10 that is coupled to the rotary dial 130. As mentioned before, the fluid transfer station 170 is used during operation of the system, at least partially, in a vial mode of operation. When the vial 60 contains only a solid medication and it is necessary for a diluent (e.g., water or other fluid) to be added to liquify the solid, this process is called a reconstitution process. Alternatively and as will be described in detail below, the medication can already be prepared and therefore, in this embodiment, the fluid transfer station is a station where a precise amount of medication is simply aspirated or withdrawn from the vial 60 and delivered to the syringe 10.

For purpose of illustration, the reconstitution process is first described. After having been cleaned, the vial 60 containing a prescribed amount of solid medication is delivered in the upright position to the fluid transfer station 170 by the device 530. As will be appreciated, the device 530 has a wide range of movements in the x, y and z directions and therefore, the vial 60 can easily be moved to a set fluid transfer position. At this position, the vial 60 remains upright and a fluid transfer device 580 is brought into position relative to the vial 60 so that an automated fluid transfer can result therebetween. More specifically, the fluid transfer device 580 is the main means for both discharging a precise amount of diluent into the vial 60 to reconstitute the medication and also for aspirating or withdrawing the reconstituted medication from the vial 60 in a precise, prescribed amount. The device 580 is a controllable device that is operatively connected to a control unit, such as a computer, which drives the device 580 to specific locations at selected times and controls with a high degree of precision the operation and discharge of medication. The control unit can be a personal computer that runs one or more programs to ensure the coordinated operation of all of the components of the system 100.

Figure 6:
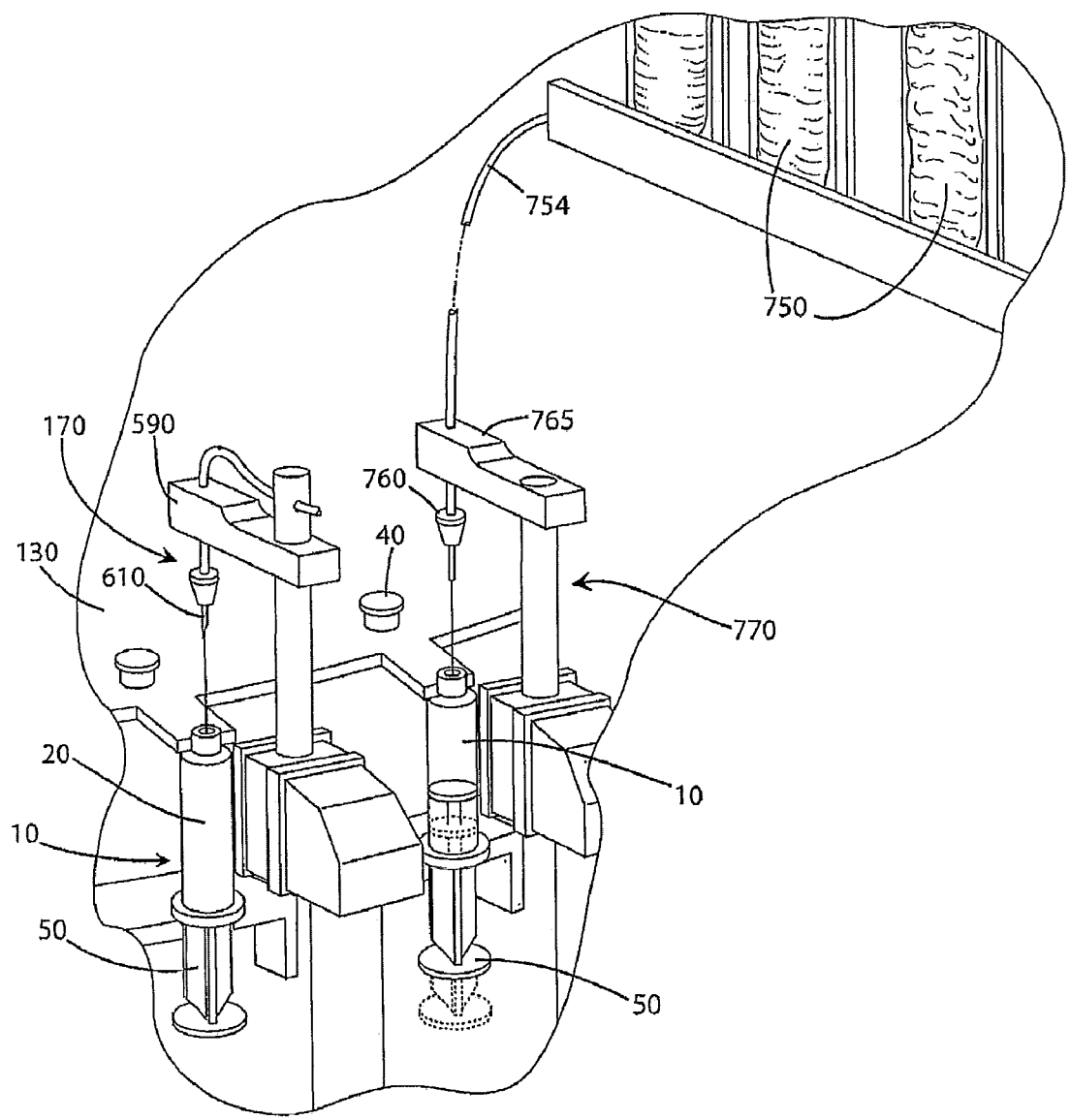
FIG. 6 is a local perspective view of first and second fluid delivery devices that form a part of the system of FIG. 2.

As illustrated in FIGS. 1 and 6, one exemplary fluid transfer device 580 is a robotic device having a movable cannula unit 590 that can be moved in a controlled up and down and side-side, etc., manner so to either lower it or raise it relative to the vial 60 in the fluid transfer position and to move it into the proper position. For example, the cannula unit 590 can be pneumatically operated or operated by an electric motor or some other means to cause the controlled movement of the cannula unit 590.

At one end of the cannula unit 590, a cannula 610 is provided. The cannula 610 has one end that serves to pierce the septum of the vial 60 and an opposite end that is connected to a main conduit 620 that serves to both deliver diluent to the cannula 610 and ultimately to the vial 60 and receive aspirated reconstituted medication from the vial 60. Preferably, the cannula 610 is of the type that is known as a vented cannula which can be vented to atmosphere as a means for eliminating any dripping or spattering of the medication during an aspiration process. More specifically, the use of a vented needle to add (and withdraw) the fluid to the vial overcomes a number of shortcoming associated with cannula fluid transfer and in particular, the use of this type of needle prevents backpressure in the vial (which can result in blow out or spitting or spraying of the fluid through the piercing hole of the cannula). The venting takes place via an atmospheric vent that is located in a clean air space and is formed in a specially designed hub that is disposed over the needle. By varying the depth that the needle penetrates the vial, the user can control whether the vent is activated or not. It will be appreciated that the venting action is a form of drip control (spitting) that may otherwise take place. Drip control is a process after aspiration where fluid is sucked back into the cannula 610 (tube) to prevent dripping of the drug and then the cannula 610 is transferred to the syringe for dispensing.

Moreover, the cannula 610 is also preferably of the type that is motorized so that the tip of the cannula 610 can move around within the vial 60 so that cannula 610 can locate and aspirate every last drop of the medication. In other words, the cannula 610 itself is mounted within the cannula unit 590 so that it can move slightly therein such that the tip moves within the vial and can be brought into contact with the medication wherever the medication may lie within the vial 60. Thus, the cannula 610 is driven so that it can be moved at least laterally within the vial 60.

An opposite end of the main conduit 620 is connected to a fluid pump system 630 that provides the means for creating a negative pressure in the main conduit 620 to cause a precise amount of fluid to be withdrawn into the cannula 610 and the main conduit 620, as well as creating a positive pressure in the main conduit 620 to discharge the fluid (either diluent or medication) that is stored in the main conduit 620 proximate the cannula 610. One exemplary fluid pump system 630, as well as the operation thereof, is described in great detail in the '823 patent, which has been incorporated by reference. The net result is that the prescribed amount of diluent that is needed to properly reconstitute the medication is delivered through the cannula 610 and into the vial 60. Accordingly, the cannula 610 pierces the septum of the vial and then delivers the diluent to the vial and the vial 60 can be inverted to cause agitation and mixing of the contents of the vial or the vial can be delivered to a separate mixing device to cause the desired mixing of the contents.

After the medication in the vial 60 has been reconstituted as by inversion of the vial and/or mixing, as described herein, the fluid pump system 630 is then operated so that a prescribed amount of medication is aspirated or otherwise drawn from the vial 60 through the cannula 610 and into the main conduit 620. Before the fluid is aspirated into the main conduit 620, an air bubble is introduced into the main conduit 620 to serve as a buffer between the diluent contained in the conduit 620 to be discharged into one vial and the aspirated medication that is to be delivered and discharged into one syringe 10. It will be appreciated that the two fluids (diluent and prepared medication) can not be allowed to mix together in the conduit 620. The air bubble serves as an air cap in the tubing of the cannula and serves as an air block used between the fluid in the line (diluent) and the pulled medication. According to one exemplary embodiment, the air block is a $\frac{1}{10}$ ml air block; however, this volume is merely exemplary and the size of the air block can be varied.

After aspirating the medication into the main conduit 620, the fluid transfer device 580 is rotated as is described below to position the cannula 610 relative to one syringe 10 that is nested within the rotary dial 130. The pump mechanism 630 is actuated to cause the controlled discharge of the prescribed amount (dosage) of medication through the cannula 610. As the pump mechanism 630 is operated, the air block continuously moves within the main conduit 620 toward the cannula 610. When all of the pulled (aspirated) medication is discharged, the air block is positioned at the end of the main conduit signifying that the complete pulled medication dose has been discharged; however, none of the diluent that is stored within the main conduit 620 is discharged into the syringe 10 since the fluid transfer device 580, and more particularly, drivers or the like of the system, operate with such precision that only the prescribed medication that has been previously pulled into the main conduit 620 is discharged into the vial 60.

It will be appreciated that the fluid transfer device 580 may need to make several aspirations and discharges of the medication into the vial 60 in order to inject the complete prescribed medication dosage into the vial 60. In other words, the cannula unit 590 can operate to first aspirate a prescribed amount of fluid into the main conduit 620 and then is operated so that it rotates over to and above one syringe 10 on the rotary dial 130, where one incremental dose amount is discharged into the vial 60. After the first incremental dose amount is completely discharged into the syringe 10, the cannula unit 590 is brought back the fluid transfer position where the fluid transfer device is operated so that a second incremental dose amount is aspirated into the main conduit 620 in the manner described in detail hereinbefore. The cannula unit 590 is brought back to the rotary dial 130 above the syringe 10 that contains the first incremental dose amount of medication. The cannula 610 is then lowered so that the cannula tip is placed within the interior of the syringe 10 and the cannula unit 590 is operated so that the second incremental dose amount is discharged into the syringe 10. The process is repeated until the complete medication dose is transferred into the syringe 10.

It will further be appreciated that the cannula unit 590 can be configured so that it can be operated at varying speeds of aspiration. For example, the software associated with the cannula unit 590 can offer the operator a number of different aspiration programs to choose from or the operator can program the unit 590 with a unique aspiration process or program by entering or inputting aspiration instructions. For example, the unit 590 can operate by first aspirating the medication at a first speed and for a first time period and then aspirating the medication at a second speed for a second time period. According to one embodiment, the first speed is greater than the second speed and the first time period is greater than the second time period; however, the opposite can be equally true and it will further be appreciated that there may be more than 2 distinct aspiration phases. For example, there can be a first aspiration phase that operates at a first aspiration speed, a second aspiration phase that operates at a second speed and a third aspiration phase that operates at a third aspiration speed. The speed of the aspiration can be varied by simply varying the speed of the pump. In this manner, the initial aspiration of the medication can operate at a higher speed and then when only a small amount of medication remains, the aspiration speed can be reduced so as to controllably withdraw the last portion of the medication that is contained in the container.

In addition, the reconstitution equipment, including the cannula unit 590, can possess various motions, including a gentle inversion to "wet" the solid drug in the vial 60 with the diluent that was added to the vial 60 and an agitation motion which causes the drug to go into solution. The system 100, and in particular, the reconstitution module thereof, is configured to operate in this manner since the reconstitution process uses both motions based upon key drug characteristics. A database controls the differences observed from drug to drug. In one embodiment, the robotic gripper holds the drug vial 60 during the agitation cycle so that is does not become dislodged. The associated software preferably possesses a QA function that enables the drug to be tested under various conditions to assure that the settings effect putting the drug into solution, and the ability to have the reconstituted drug manually observed, by the robotic gripper removing the drug from the reconstitution station 170 and presenting the vial 60 to a window (when the system 100 is contained within an enclosed structure as described below) for an operator to look at the vial 60 and enter their observations into a reconstitution QA database. If the drug was not fully in solution, the entry into the QA database can be used to adjust the formulary to require an additional increment of agitation time.

In other words, the software is designed so that once the operator enters the drug order, the master controller accesses the reconstitution database that includes detailed instructions as to how to prepare the reconstituted drug of the order and part of these instructions include instructions on the aspiration process as discussed below. In particular, once the drug type of the order is identified, the aspiration instructions are determined, including the number, length and characteristics of the agitation phases and motions, and then the controller instructs the equipment to execute these instructions.

In yet another embodiment, a prescribed dosage of medication can be drawn from the vial 60 by mating a syringe 10 with the vial 60 as by inserting the needle (vented cannula) of the syringe into and through the septum of the vial 60 and then extending the plunger a predetermined, precise distance so as to draw a precise amount dosage into the syringe from the drug vial 60. The device and method for controlling the extension of the plunger is described in great detail herein.

Once the syringe 10 receives the complete prescribed medication dose, the vial 60 that is positioned at the fluid transfer position can either be (1) discarded or (2) it can be delivered to a holding station 700 where it is cataloged and held for additional future use. More specifically, the holding station 700 serves as a parking location where a vial that is not completely used can be used later in the preparation of a downstream syringe 10. In other words, the vials 60 that are stored at the holding station 700 are labeled as multi-use medications that can be reused. These multi-use vials 60 are fully reconstituted so that at the time of the next use, the medication is only aspirated from the vials 60 as opposed to having to first inject diluent to reconstitute the medication.

The user can easily input into the database of the master controller which medications are multi-use medications and thus when the vial 60 is scanned and identified prior to being delivered to the fluid transfer position, the vial 60 is identified and marked as a multi-use medication and thus, once the entire medication dose transfer has been performed, the vial gripper device 530 is instructed to deliver the vial 60 to the holding station 700. Typically, multi-use medications are those medications that are more expensive than other medications and also are those medications that are used in larger volumes (quantities) or are stored in larger containers and therefore come in large volumes.

The holding station 700 is simply a location where the multi-use vials can be easily stored. For example, the holding station 700 is preferably a shelf or even a cabinet that contains a flat surface for placing the vials 60. Preferably, there is a means for categorizing and inventorying the vials 60 that are placed at the holding station 700. For example, a grid with distinct coordinates can be created to make it easy to determine where each vial 60 is stored within the holding station 700.

Once the device 530 has positioned the vial 60 at the proper location of the holding station 700, the gripper unit is operated so that the arms thereof release the vial 60 at the proper location. The device 530 then returns back to its default position where it can then next be instructed to retrieve a new vial 60 from the pedestal 520.

If the vial 60 is not a multi-use medication, then the vial 60 at the fluid transfer position is discarded. When this occurs, the device 530 moves such that the vial 60 is positioned over a waste chute or receptacle and then the gripper unit is actuated to cause the vial 60 to drop therefrom into the waste chute or receptacle. The device 530 is then ready to go and retrieve a new vial 60 that is positioned at the pedestal 520 for purposes of either reconstituting the medication or simply aspirating an amount of medication therefrom or a vial from the holding station 700 can be retrieved.

As previously mentioned, during the reconstitution process, it is often necessary or preferable to mix the medication beyond the mere inversion of the vial and therefore, the vial 60 can be further agitated using a mixing device or the like 710. In one embodiment, the mixing device 710 is a vortex type mixer that has a top surface on which the vial 60 is placed and then upon actuation of the mixer, the vial 60 is vibrated or otherwise shaken to cause all of the solid medication to go into solution or cause the medication to be otherwise mixed. In yet another embodiment, the mixing device is a mechanical shaker device, such as those that are used to hold and shake paint cans. For example, the vial 60 can be placed on support surface of the shaker and then an adjustable hold down bar is manipulated so that it travels towards the vial and engages the vial at an end opposite the support surface. Once the vial 60 is securely captured between these two members, the shaker device is actuated resulting in the vial 60 being shaken to agitate the medication and ensure that all of the medication properly goes into solution. In addition, the mixing device 710 can also be configured so that it is in the form of a robotic arm that holds the vial by means of gripper members (fingers) and is operatively connected to a motor or the like which serves to rapidly move the arm in a back and forth manner to cause mixing of the medication.

In yet another embodiment, reconstitution is done using a process commonly called "milking". In this process, diluent is added to the drug vial to be reconstituted and with a series of "pull and push" motions of fluid, reconstitution is achieved. In this process, a non-venting needle is used.

Figure 18:
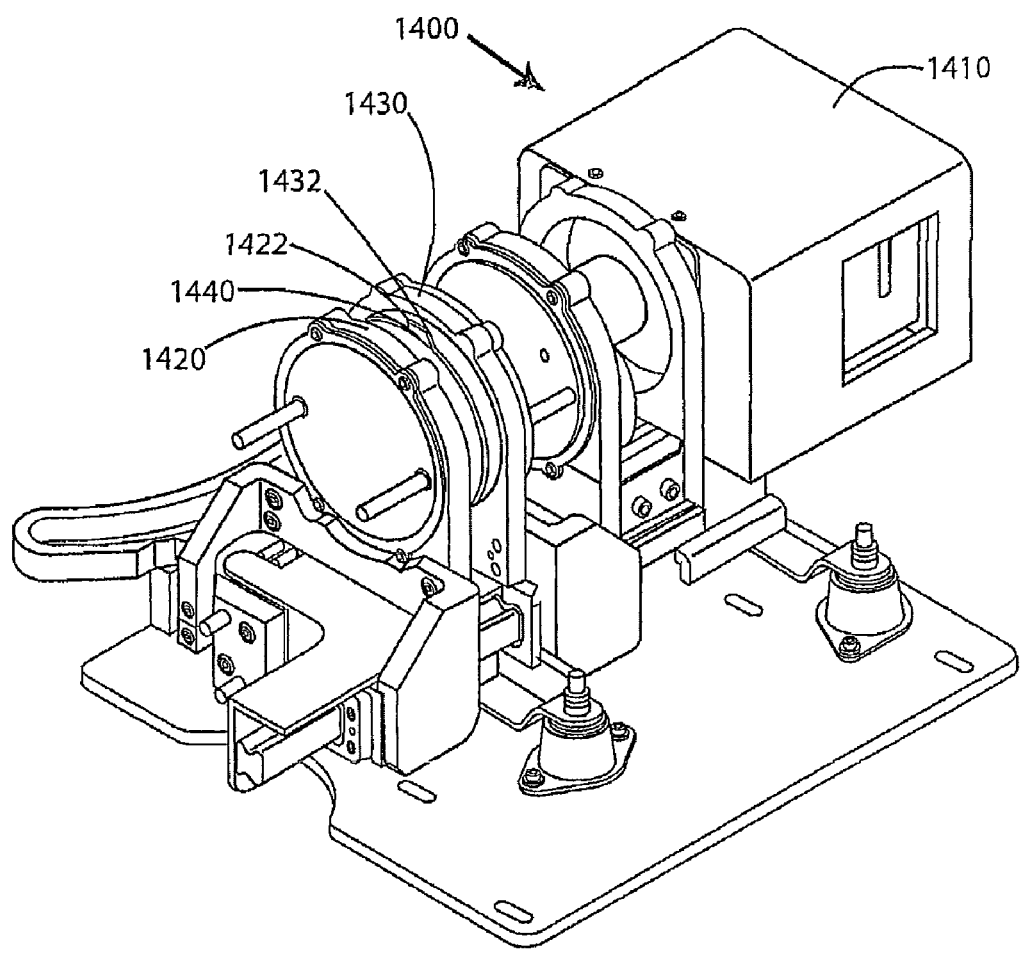
FIG. 18 is a perspective view of a vibratory vial reconstitution system for holding and mixing a drug vial.

FIG. 18 shows yet another device for mixing the contents of the drug vial. In particular, FIG. 18 shows a vibratory reconstitution system 1400 that receives and holds a vial containing solid medication mixed with diluent and is configured to be controllably actuated to cause mixing of the diluent and solid medication. The system 1400 includes an actuator 1410, such as a motor, and a first plate 1420 and a second plate 1430 that face one another and are constructed to receive a drug vial therebetween in a grasped manner.

More specifically, the first plate 1420 includes a first feature 1422 and the second plate 1430 includes a second feature 1432 that face each other and define a cavity 1440 that receives and holds the drug vial. In the illustrated embodiment, the first plate 1420 and the second plate 1430 each has a circular shape. The first and second plates 1420, 1430 can move in unison so as to permit the controlled mixing of the drug vial that is captured between the plates 1420, 1430. The plates 1420, 1430 are operably coupled to the motor 1410 to allow controlled movement of the plates 1420, 1430. It will therefore be appreciated that the motor 1410 can be a multi-speed motor or otherwise have multiple different modes of operation to permit controlled wetting or mixing of the drug vial. For example, in one mode, the contents of the drug vial are wetted by causing rotation of the first and second plates 1420, 1430 to cause the diluent in the drug vial to come into contact with the solid in the drug vial resulting in wetting of the contents. In addition, the first and second plates 1420, 1430 can be operated in a mixing mode in which the plates 1420, 1430 oscillate or otherwise move (impart vibrations) to cause a mixing of the contents of the drug vial.

It will be understood that the system 1400 is not limited to being used with the drug vial but instead, the system 1400 can receive and hold a syringe (drug delivery device) and therefore, function as a holding station or parking station where the syringe is held in place until time for delivering the syringe to a next station by means of a robotic device or the like.

As briefly mentioned before, the entire system 100 is integrated and automated and also utilizes a database for storing identifying data, mixing instructions, and other information to assist in the preparation of the medication. There are also a number of safety features and check locations to make sure that the medication preparation is proceeding as it should.

For example, the database includes identifying information so that each vial 60 and syringe 10 can be carefully kept track of during each step of the process. For example, the reader (e.g., barcode scanner or camera) 151 and the photoimaging equipment serve to positively identify the vial 60 that is delivered from the drug storage 110. Typically, the user will enter one or more medication preparation orders where the system 100 is instructed to prepare one or more syringes that contain specific medication. Based on this entered information or on a stored medication preparation order that is retrieved from a database, the vial master controller determines at which location in the cabinet the correct vial 60 is located. That vial 60 is then removed using a robotic gripper device (not shown) and is then placed on the conveyor belt 111 and delivered to the mechanism 510 pivots upright so that the vial 60 is moved a vertical position relative to the ground and is held in an upright manner and is then delivered to the rotatable pedestal 520. At the pedestal 520, the vial 60 is scanned to attempt to positively identify the vial 60 and if the scanned identifying information matches the stored information, the vial 60 is permitted to proceed to the next station. Otherwise, the vial 60 is discarded.

Once the vial 60 is confirmed to be the right vial it proceeds to the fluid transfer position. The master controller serves to precisely calculate how the fluid transfer operation is to be performed and then monitors the fluid transfer operations has it is occurring. More specifically, the master controller first determines the steps necessary to undertake in order to perform the reconstitution operation. Most often during a reconstitution operation, the vial 60 that is retrieved from the drug storage 110 contains a certain amount of medication in the solid form. In order to properly reconstitute the medication, it is necessary to know what the desired concentration of the resulting medication is to be since this determines how much diluent is to be added to the vial 60. Thus, one piece of information that the user is initially asked to enter is the concentration of the medication that is to be delivered to the patient as well as the amount that is to be delivered. Based on the desired concentration of the medication, the master controller is able to calculate how much diluent is to be added to the solid medication in the vial 60 to fully reconstitute the medication. Moreover, the database also preferably includes instructions as to the mixing process in that the mixing device is linked to and is in communication with the master controller so that the time that the mixing device is operated is stored in the database such that once the user inputs the medication that is to be prepared and once the vial 60 is scanned and identified, the system (master controller or CPU thereof) determines the correct of time that the vial 60 is to be shaken to ensure that all of the medication goes into solution.

Once the master controller determines and instructs the working components on how the reconstitution operation should proceed, the master controller also calculates and prepares instructions on how many distinct fluid transfers are necessary to deliver the prescribed amount of medication from the vial 60 to the syringe 10. In other words, the cannula unit 590 may not be able to fully aspirate the total amount of medication from the vial 60 in one operation and therefore, the master controller determines how many transfer are needed and also the appropriate volume of each aspiration so that the sum of the aspiration amounts is equal to the amount of medication that is to be delivered to the syringe 10. Thus when multiple aspiration/discharge steps are required, the master controller instructs and controls the operation of the pump mechanism so that the precise amounts of medication are aspirated and then discharged into the syringe 10. As previously described, the pump mechanism operates to cause the proper dose amount of the medication to be first aspirated from the vial and then discharged into the syringe. This process is repeated as necessary until the correct dose amount is present in the syringe 10 in accordance with the initial inputted instructions of the user. Yet in another embodiment, multiple doses are aspirated from the vial and smaller doses are dispensed into multiple syringes.

After transferring the proper precise amount of medication to one syringe 10, the master controller instructs the rotary dial to move forward in an indexed manner so that the next empty syringe 10 is brought into the fluid transfer position. The cannula 610 is also preferably cleaned after each medication dose transfer is completed so as to permit the cannula 610 to be reused. There are a number of different techniques that can be used to clean the cannula 610 between each medication transfer operation. For example, the cleaning equipment and techniques described in commonly assigned U.S. Pat. No. 6,616,771 and U.S. patent application Ser. No. 10/457,898 (both of which are hereby incorporated by reference in their entireties) are both suitable for use in the cleaning of the cannula 610.

In one embodiment, the cannula 610 is rotated and positioned so that the needle of the cannula 610 is lowered into a bath so that fluid is expelled between the inside hubs of the syringe 10 for cleaning of the interior components of the cannula 610. The cannula 610 is then preferably dipped into a bath or reservoir to clean the outside of the cannula 610. In this manner, the cannula 610 can be fully cleaned and ready for a next use without the need for replacement of the cannula 610, which can be quite a costly endeavor.

In yet another embodiment, a medication source, such as a bag that is filled with liquid medication that has already been properly reconstituted, is connected to an input portion of a peristaltic pump by means of a first conduit section. A second conduit section is connected to an output port of the pump and terminates in a connector. The connector is of the type that is configured to hermetically seal with an open barrel tip of the syringe 10 that is nested within the rotary dial 130 and is marked to receive medication. The connector typically includes a conduit member (tubing) that is surrounded by a skirt member or the like that mates with the outer hub of the syringe barrel. A flange or diaphragm can be provided for hermetically sealing with the syringe barrel (outer hub).

Figure 14:
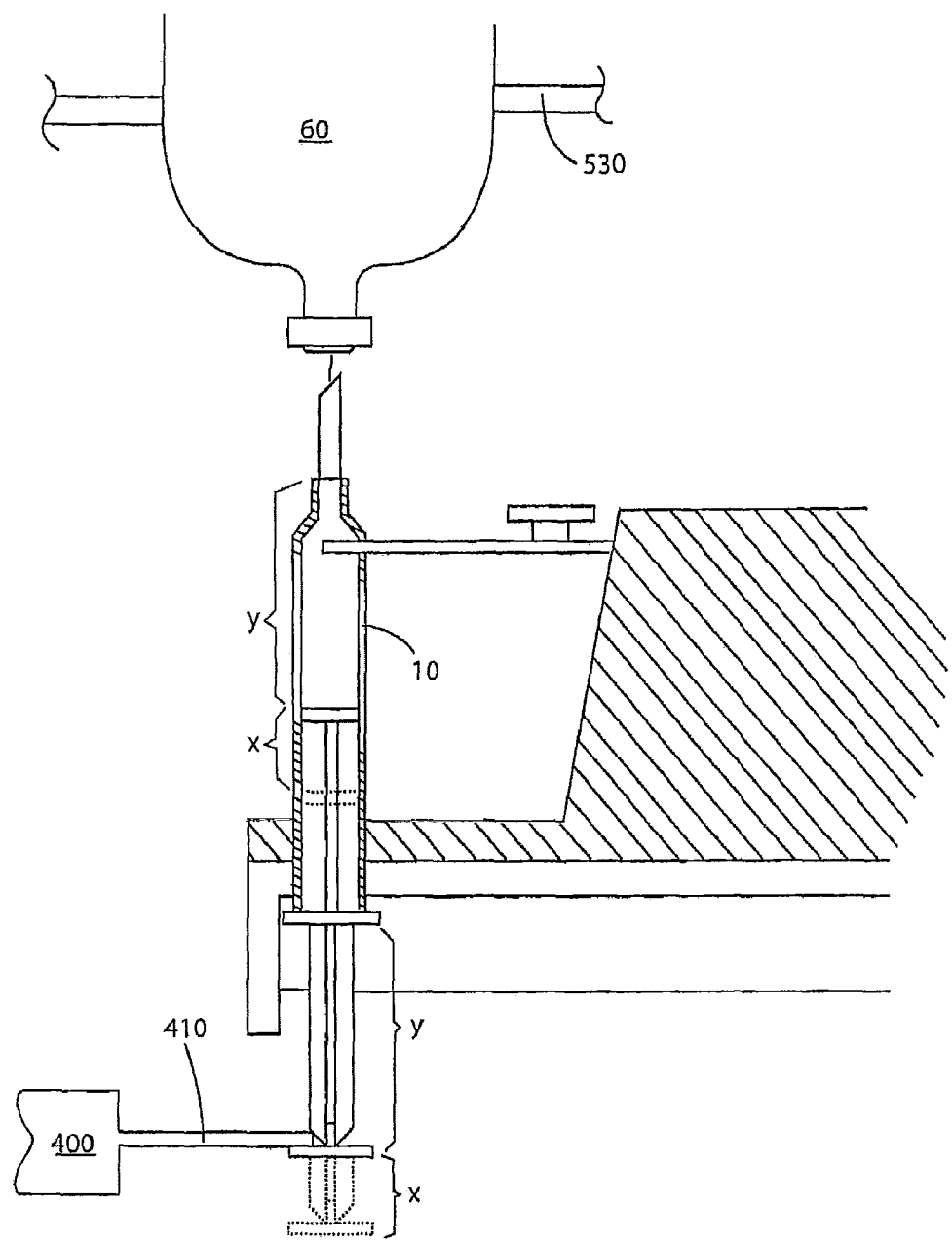
FIG. 14 is a cross-sectional view of drug delivery directly from a drug vial by extending the plunger of a syringe with an automated mechanism.

In commonly assigned U.S. patent Ser. No. 11/434,850 (which is hereby incorporated by reference in its entirety), it is described how the plunger 50 of the syringe 10 can be extended with precision to a prescribed distance. In that application, the plunger 50 is extended to create a precise volume in the barrel that is to receive a precise prescribed dosage of medication that is injected therein at a downstream location. However, it will be appreciated that the action of extending the plunger 50 can serve more than this purpose since the extension of the plunger 50 creates negative pressure within the syringe barrel and thus can serve to draw a fluid therein. For example, once the connector is sealingly mated with the open syringe tip end, the medication source (e.g., an IV bag) is fluidly connected to the syringe 10 and thus can be drawn into the syringe barrel by means of the extension of the plunger 50. In other words, the plunger 50 is pulled a precise distance that results in the correct size cavity being opened up in the barrel for receiving the fluid but also the extension of the plunger creates enough negative pressure to cause the medication to be drawn into the syringe barrel. This is thus an alternative means for withdrawing the proper amount of medication from a member (in this case the source) and transferring the desired, precise amount of medication to the syringe 10. The operation of this alternative embodiment can be referred to as operating the system in reservoir mode and is shown in FIG. 14. One advantage of this embodiment is that multiple syringe drivers or the like or some type of pump mechanism are not needed to pump the medication into the syringe 10 but rather the drawing action is created right at the rotary dial 130. This design is thus fairly simple; however, it is not suitable for instances where drug reconstitution is necessary.

It will also be appreciated that the source does not have to be a medication source in that it does not have to contain an active drug but instead, the source can contain diluent that is to be drawn in a prescribed volume into the syringe, especially for purposes of serial dilution, as described below. More specifically and as illustrated in FIGS. 1 and 6, in the reservoir mode, the fluid source can consist of a number of drug delivery bags 750 that are already filled either premixed medication or with only diluent that is later used to dilute medication as described in detail below. The filled drug delivery bags (e.g., IV bags) 750 can be hung in a select area, with each bag 750 having an outlet conduit through which the fluid contained in the bag is drawn. It will be appreciated that the outlet conduits associated with the drug delivery bags 750 can be interconnected as by connecting each of the bag outlet conduits to a common line 754 with one or more valves or the like being used to selectively control which bag outlet line is in directly fluid communication with the common line 754. In this manner, a number of different medications can be hung and be ready for use and the user of the system merely has to manipulate the valve (either manually or automatically using a computer, etc.) to connect the selected bag 750 to the common line 754.

The computer that operates the entire system can be in communication with the valves to permit and to control the flow of the prescribed desired fluid from one bag 750 to the common line 754. The common line 754 is thus in communication at a first end with the outlet conduit of the select bag 750 that contains the desired fluid and another end of the common line 754 is configured to mate with a syringe inlet port to permit the fluid in the bag 750 to be drawn into the bag by extending the plunger 50 a predetermined distance as described above to cause a precise, target volume of fluid to be drawn into the barrel of the syringe 10. For example, the free end of the common line (conduit) 754 can contain a connector or adapter (e.g., a stopper element) 760 that is configured to mate with the inlet opening (port) of the syringe barrel in a sealed manner. Since it is the extension of the plunger 50 that generates the means of drawing a prescribed volume of fluid into the syringe barrel, the connection between the end of the common line (e.g., the connector thereof) and the syringe barrel is such that the creation of negative pressure in the syringe barrel 20 causes the fluid to be drawn into the barrel. In other words, it is desirable to establish a seal or the like between the end of the common line 754 and the syringe barrel so that negative pressure can be established and maintained in the syringe barrel.

For purpose of illustration, the delivery of fluid from one source during operation of the reservoir mode to one syringe 10 is performed at the reservoir mode fluid delivery station 770 that is arranged relative to the other stations of the system 100.

According to one embodiment, the free end of the common line 754 is secured to a controllable, movable device, 765 such as a robotic arm or an automated arm, that can be controllably moved. In particular, the movable device is moved vertically at least along a linear axis so as to drive the free end of the common line 754 (the connector) into a sealed coupling with the syringe barrel when it is driven in one direction or when it is driven in the opposite direction, the common line disengages from the barrel of the syringe 10 to permit the syringe to be advanced to another station, such as the fluid transfer station 170 described above where reconstituted drug can be delivered into a syringe 10 that was previously injected with fluid through the common line 754 from the fluid source when operating in reservoir mode.

It will be appreciated that the reservoir drug delivery station 770 and the fluid transfer station 170 are different stations that are located at different locations, such as adjacent stations along the dial 130.

According to one aspect of the present invention, a serial dilution operation can be performed by the system 100 by performing one or more operations at the reservoir drug delivery station 770, where fluid is delivered to a syringe from a source, such as one bag 750, and the drug delivery station 170 where a drug can be reconstituted in a drug vial 60 before injection into a drug delivery device (syringe 10). Preferably, the station 170 is downstream of the station 770 so that loaded syringes 10 are first processed at station 770 and then is processed at station 170. In general, serial dilution involves and provides a process by which a commercially available injection is diluted to a lower concentration to produce doses smaller than could otherwise be measured by the device that prepares the medication. Pediatric hospitals often must produce doses of injectable medications that are immeasurably small when prepared with commercially available medications. This requires that the drug therefore be diluted to a concentration where the required dose becomes measurable. This can require one or more dilution steps to reach a required concentration.

The system 100 of the present invention, along with other similar devices, has practical measurement limitations based on its delivery technology. For example, doses that are aspirated from a vial with a pump, such as a Kloehn type pump, at the drug delivery station 170 can be reliably measured down to a volume of 0.5 ml; doses delivered at the reservoir mode drug delivery station 770 from the reservoir (bag 750) can be accurately delivered down to a volume of approximately 2 ml with a ±0.125 ml margin of error.

Since the reservoir mode is designed to batch fill a series of identical syringes 10, reservoir mode restrictions can be overcome in the process of preparing the reservoir itself. That is, the reservoir can be prepared in a more dilute state, and any dilution necessary to achieve the final concentration are performed during preparation of the reservoir prior to mounting the reservoir (bag) within the system 100 at the station 770.

When a syringe 10 is prepared from a vial 60, as in reconstitution mode, at the drug delivery station 170, it is ordinarily filled from the vial at its commercial concentration, which can be determined at the manufacturer (because it is already a liquid) or can be determined by the reconstitution for the vial in the formulary. If further dilution is required, it cannot be performed in advance because doing so severely limits the shelf of the product. It must either be diluted in the syringe 10 (this is referred to as QSing the syringe 10), or the additional dilution must be prepared "on the fly" within the system 100. Currently, there is a mechanism to perform additional dilution in the syringe 10, but there is no mechanism to perform additional dilution in another vial.

The solution to the above deficiency that is achieved and provided by the system 100 is to permit the system 100 itself to prepare a dilution as needed. The process involves having the system 100 prepare an injectable product by further diluting the original available product and then using the dilution to prepare the dose. The system 100 is thus configured to store and manipulate sterile empty vials 60 within the vial cabinet at station 110, and to maintain knowledge of both the original and diluted products until they are discarded or consumed.

In other words, if the manufacturer's product is available as a fluid, of concentration X, and the dose required a concentration X/10, the software would cause the device to aspirate 1 ml of the original drug from the original container, deliver that 1 ml into an empty container, and then deliver 9 ml of diluent to product a final concentration of X/10. This presumes that the original drug solution and the diluent mix volumetrically (e.g., that 1 ml of drug and 9 ml of diluent mix to create a total volume of 10 ml). In practice, pediatric applications can require dilutions of 10- to 30-fold. The requirement for the ability to perform dilutions must accommodate the fact that not all immeasurable doses are intended since a dose may be immeasurable because it was entered incorrectly. Since, in at least one embodiment of the system 100, the system 100 lacks the information necessary to determine whether a dose is clinically appropriate for a given patient, the system 100 is configured to permit dilution only when one is required to prepare a dose in measurable range and there is a pre-defined dilution product that can be prepared from a commercially available product defined for that purpose in the formulary.

For the purpose of the present application, the term "parent vile" refers to a vial containing a commercially available concentration of a drug that is either supplied as a fluid from the manufacturer, or was reconstituted according to its formulary definition within the system 100. The term "child vial" refers to a vial containing a concentration of a drug that is not commercially available that is prepared by diluting an aliquot from a parent vial with sufficient diluent to create a new, lower concentration of drug.

According to one embodiment of the present invention and based on the specifications of one system 100, preparation of the diluted product is required if at least one syringe requires a dose volume of less than 0.5 ml from the parent drug. For example, if a syringe 10 requires a 1:10 dilution for a 2 ml dose, the 0.2 ml to be taken from the parent vial is too small. As a result, if dilution is required, then it is preferred to use up the dilution before using up the contents in the parent vial. This can be accomplished by sorting the syringes within a drug in ascending order by dose. This way, the smaller doses will force creation of the diluted product (if required) and subsequent syringes 10 will use that product until it is consumed.

One will appreciate that there is a parent-child relationship between the diluted product and the non-diluted product from which it can be made. The commercially available product from which the dilution is to be prepared is the parent and the resulting diluted drug solution is the child. The process of creating the child product should be sufficiently flexible that the system 100 is able to use the best available parent for the process and in particular, the system 100 (and the software thereof) is able to handle the following scenarios: (1) there is no parent vial already available on the hold location—the software should drop a new parent vial from the drug cabinet 110 choosing the smallest vial that can deliver the quantity of parent medication needed to prepare the child; (2) there is no parent vial available on the hold location—there are additional syringes that will be prepared directly from the parent vial, in which case the software of the system 100 should drop a new parent vial from the drug cabinet 110 choosing the smallest vial that can deliver the quantity of parent medication needed to prepare the child and the additional syringes; (3) a parent vial for the drug to be diluted is already on the hold location and has sufficient supply to create the dilution—the software of the system 100 should use the parent vial on the hold location to prepare the child; and (4) a parent vial for the drug to be diluted is already on the hold location and does not contain sufficient drug to prepare the child—the software should drop a new parent vial from the drug cabinet and should choose the smallest vial that will permit preparation of the child. These aspects of the present system 100 are described in greater detail below.

According to one embodiment of the present invention, the system 100 includes a method of dilution in which a formulary contains a product definition and a container definition for each child product (dilution) that can be prepared by the system 100. For example, a Clindamycin 5 mg/ml dilution in a 30 ml vial will exist in the formulary as Clindamycin 150 mg container and a Clindamycin 5 mg/ml, 30 ml product vial. The vial product will be a specially marked product whose formulary definition contains: (i) the product ID of a commercially available product from which it is prepared, (ii) the volume of the commercial product needed to prepare the dilution, and (iii) a volume of diluent needed to prepare the final dilution.

The system 100 and in particular, the inventory tracking software thereof, assigns each child product to a specific column in the drug cabinet 110. That column in the drug cabinet 110 stores a sterile, empty vial for use in preparing the dilution that is labeled with the drug name, concentration, volume and bar code. The system 100 includes a vial routine that assigns a vial to a syringe 10 when it is loaded onto the dial 130 and has additional logic that determines vial suitability based on the dose volume and concentration. This routine of the system 100 searches each product in the inventory for the requested drug and then select the product that will provide the drug in the smallest measurable volume.

If the selected drug is a dilution, the software of the system 100 will first cause the automated components of the system 100 to locate and acquire the parent commercially available vial, reconstitute it, if necessary, aspirate the defined volume from the parent vial and then park the parent vial in an available hold location. If there are previously loaded syringes 10 that will use an already-defined child vial that has not yet been created but for which the entire vial has not been committed, the software will assign the syringe 10 to that vial 60. If there is already a vial 60 on a hold location (station 700) that contains the same drug in the same concentration as the designated parent vial, the software will use the vial on the hold location to prepare the child. If there are previously loaded, unfilled syringes that are to be filled from the parent vial directly, and there is spare capacity in the parent vial, the software of the present system 100 prepares the child from the parent vial assigned to those previously loaded syringes 10. If a new child vial is needed, and a new parent vial is needed, the software of the system 100 will query the queue for other syringes that can be prepared from the parent vial. If a new child vial is needed, and a new parent vial is needed, and no other parent supply is needed, the software will drop a parent vial as the assigned parent from the formulary. If the particular assigned parent is not available, the software of the system 100 locates another vial of the same drug and concentration that can be used to prepare the child.

The software of the present invention then causes the automated system 100 to "drop" an empty vial from the dilution product volume, and inject the defined volume of drug followed by the required amount of diluent to prepare the requested dilution. To speed up the operation, the parent vial can be agitating while the empty is vial is dropped and verified. If a child already exists on the hold location and it has available capacity, no new child vial is dropped from the drug cabinet 110. If the child vial is not on the hold location, or if such a vial on the hold location lacks capacity to fill the syringe 10, the software of the system 100 drops a new child vial and prepares it from the parent vial contents and diluent. For example, to prepare a 5 mg/ml solution of Clindamycin from a commercially available 150 mg/ml solution, the present system 100 injects 1 ml of the commercially available Clindamycin and 29 ml of diluent into a 30 ml empty vial labeled for the dilution. Similarly, to prepare a 10 mg/ml Cefazolin solution from a 1 gm/5 ml (200 mg/ml solution), the system 100 is instructed to reconstitute the Cefazolin at the fluid delivery station 170 as described herein, aspirate 1 ml from the reconstituted vial, acquire a 20 ml sterile empty vial, inject the 1 ml of Cefazolin 200 mg/ml, followed by 19 ml of water to create a 20-fold dilution. After agitating, the fluid in the mixer, the software of the present system 100 then aspirates the final dose out of the vial 60 and injects the dose into the syringe 10. Agitating the vial in the mixer or between the grippers of the robotic transporter is likely inadequate because the drug is already a liquid and would only require flipping the vial once or twice.

The above process is described in detail with reference to FIG. 15 which shows a flowchart of the dilution process. It will be appreciated that there are a number of advantages of the serial dilution capabilities of the system 100 and in particular, the serial dilution functionality permits customized drug solutions to be prepared from commercial drug solutions and the need for such customized drug preparation can be determined at run time (in real time) and if so, the automated system 100 can react to that need by preparing (if needed) the commercial drug product and then using the commercial drug product (e.g., a reconstituted medication) to prepare the custom drug solution.

It will be appreciated that in the above dilution process, each dilution consumes two positions in the "parking lot" or holding station 700, one for the parent vial and one for the diluted vial. This makes it likely that prepared dilutions that are not used immediately will be discarded before they are consumed to make way for preparation of other diluted products. One exception to this would be to store the parent vial in the mixer 710 when its not being used, especially, when the mixer 710 includes a pair of gripping elements between which the vial is received and held. If all of the drug is used up in either of the vials (parent and child), only one of the hold areas would need to be used. If both of the vials (parent and child) are used up, none of the hold areas would be used. Space in the drug cabinet 110 is to be committed for the vials labeled for the diluted product. A column will be required for each drug/concentration combination.

In another aspect of the present invention, a pharmacy-managed method for labeling sterile empty vials for use in preparation of diluted product as described above is preferable provided. The pharmacy requires a separate process for printing labels with appropriate bar codes and human-readable text on the labels, applying those labels to vials used for dilution of the correct size, and verifying that the correct labels were correctly applied.

In one embodiment of the present invention, the serial dilution functionality of the present system 100 permits definition of a product that can be prepared by diluting another product and includes the following functionality: (a) only commercially available injections can be used to prepare a dilution (that is, one cannot prepare one dilution from another dilution); (b) the software of system 100 permits dilutions up to 100-fold (e.g., a dilution containing 1 ml of commercially available drug and 99 ml diluent); (c) the system software provides traceability of both the diluted product and the parent product in a preparation history log and optionally, a verification tab of the software allows the user to view the parent vial images and child vial images; (d) the system 100 scan inventoried products and selects the product that provides the ordered drug in the smallest volume greater than or equal to 0.5 ml and less than or equal to 10 ml; (e) the system 100 determines if the total amount of the drug and diluent is less than a maximum final volume (e.g., a maximum of 11.5 ml)—and if it is, the syringe can be used to prepare the dose (this can result in mixture ratios of up to 23 to 1); (f) the system 100 shall maintain at least one column of empty vials for each dilution product and dilution ratio that can be prepared; (g) the system 100 detects the condition in which the selected product is a diluted product and shall cause the dilution to be prepared from a parent product; (h) if available, the system 100 uses a partial vial from a hold location (hold station) or from the grippers of the mixer if the vial is contained therein to prepare a diluted product; (i) if needed, the system 100 reconstitutes the parent product according to the instructions in its formulary record; (j) if needed, the system 100 clears two hold locations (at station 700) for dilution activities by removing their current occupants and placing them in the restocking bin; (k) the software of the system 100 aspirates the parent product volume from the parent vial; (l) the system 100 injects the parent product volume into the child vial; (m) the system 100 injects the prescribed diluent volume into the child vial; (n) the system 100 is configured to invert the vial three times to ensure mixing (this can be done in the grippers of the robotic device to save time or in a mixer); (o) the system 100 aspirates the required dose from the child vial and inject it into the syringe; and (p) if there is more than the minimum residual volume of the child product remaining after preparation of pending doses, the system 100 stores the child product up to its expiration time at an available location of the hold station 700.

The system 100 also is configured to reject the drug order and print a pass-through label if: (1) there is no source container that can provide the dose in a volume between 0.5 ml and 11.5 ml; (2) there is no inventory of a parent drug for a selected diluted drug; (3) there are no more vials in which to prepare a diluted drug; (4) the ordered final volume is less than the required dose volume for all available products of the specified drug.

Figure 15:
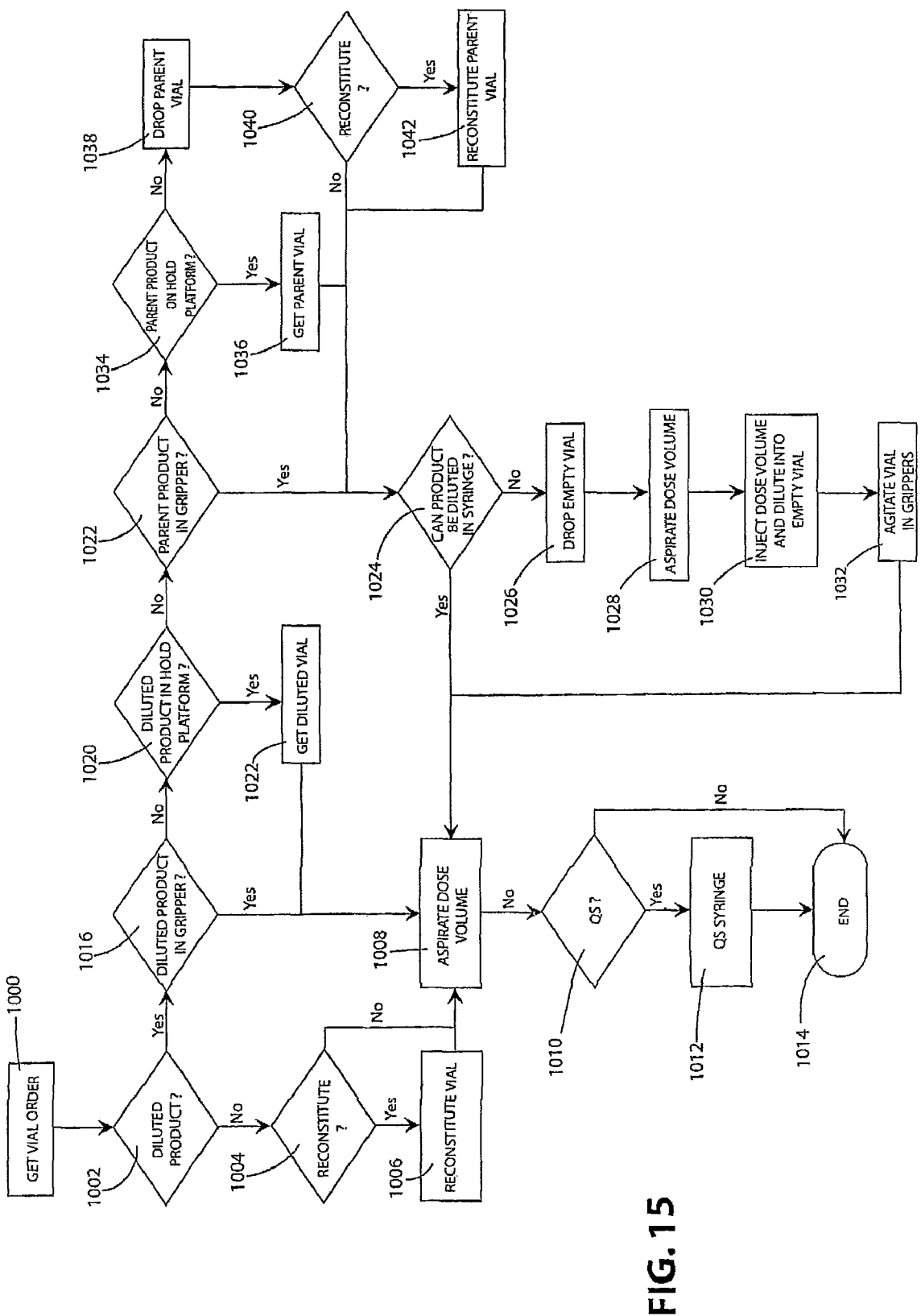
FIG. 15 is a flow chart illustrating the steps of a serial dilution performed by the devices of FIG. 6.

More specifically, FIG. 15 sets forth a flowchart detailing one exemplary process for performing serial dilution with the system 100 of the present invention at the various stations thereof. At step 1000, a vial order is received. At step 1002, it is determined whether a diluted product is needed. If the product is not a diluted product, then at step 1004, it is determined whether the drug is to be reconstituted. If the drug is to be reconstituted, then it is done so at step 1006. If the drug is not to be reconstituted, then at step 1008, a dose volume of drug is aspirated. At step 1010, it is determined whether additional dilution of the aspirated dose volume is to be performed in the syringe. If so, then the dose is diluted in the syringe itself at step 1012 and then the process ends at step 1014. If additional dilution in the syringe is not required, then the process ends at step 1014.

If at step 1002, it is determined that a diluted product is needed, then at step 1016, it is determined whether the diluted product is being held in the gripper (robotic arm or mixer). If so, then at step 1008, a dose volume is aspirated therefrom. The process then goes to step 1010, to determine whether additional dilution of the aspirated dose volume is to be performed in the syringe. If so, then the dose is diluted in the syringe itself at step 1012 and then the process ends at step 1014. If additional dilution in the syringe is not required, then the process ends at step 1014.

If the diluted product is not present in the gripper (step 1016), then the system determines at step 1020 if the diluted product is present on the hold platform (station 700). If the diluted product is at the hold platform, then a diluent vial is retrieved at step 1022 and then the process continues to steps 1008-1014.

If the diluted product is not present on the hold platform in step 1020, then the system 100 determines at step 1022 whether the parent product is being held in the gripper (robotic arm). If the answer to step 1022 is yes, then the system determines at step 1024 whether the product be diluted in the syringe (QSing the syringe) and if so, the process continues to steps 1008-1014. If the product cannot be diluted in the syringe, then at step 1026, an empty vial is dropped; at step 1028, the dose volume is aspirated from the parent product; at step 1030, the dose volume and diluent are injected into the empty vial and at step 1032, the product is agitated in the grippers before the process continues to steps 1008-1014.

If the answer to step 1022 is no, then the system determines at step 1034 whether the parent product is present on the hold platform (station 700) and if so, then at step 1036, the parent vial is retrieved from the hold platform before process continues to step 1024. If the answer to step 1034 is no, then the parent vial is dropped at step 1038 and at step 1040, it is determined whether to reconstitute the drug. If the drug is to be reconstituted, then it is done so at step 1042 before the process continues to step 1024. If the drug is not to be reconstituted, the process continues to step 1024.

FIG. 16 shows an exemplary computer screen display 1100 for entering diluted product information. In this example, a diluted product is being added to the software and in particular, in box 1101, the user enters a drug description, in this case, "Oxacillin 100 mg Dilution" and then the user in box 1102 selects an appropriate drug container, in this case, "Oxacillin 100 mg". In box 1104, the user enters a unique drug code, in this case, "12345678" and in box 1106, a bar code for the diluted product is entered, in this case "12345678". In box 1107, the reconstituted volume is entered, in this case, 10 ml and in box 1108, the reconstituted concentration is added, in this case, 10 mg/ml. To add this product to the software, a button 1110, such as an Add button, is selected.

After this information is inputted, a series of formulary tests for the diluted product entry is performed and in particular, the drug name is looked up from the container. The system 100 searches all products which are not dilutions and are the specified drug. A search is also performed for a dilution ratio, such as a ratio between $1 \leq ratio \leq 100$ (the ratio is equal to the concentration of the parent/concentration of child in base units). A first match is accepted on the first round if it passes all quality control inquiries. It will also be appreciated that the software can be configured so that a formulary product editor and verify screens shall limit the products that can be used to serve as parent products to those that do not have the dilution field selected as TRUE (products that are commercially available and are not diluted products). Safety feature are preferably incorporated into the software to restrict the manner in which a formulary upgrade is performed. For example, an updated product file shall require verification by a user, who is allowed to verify formulary changes (e.g., a pharmacist), before the update can be completed.

After the medication is aspirated into the barrel 20, the dial 130 is advanced so that the filled syringe 10 is delivered to the sixth station 180 (FIG. 2). For example, the dial 130 is preferably advanced so that the filled syringe 10 is delivered to a station where the removed tip cap 40 is replaced back onto the barrel tip 28 by a device 900. The device 900 can be similar or identical to the device 300 that removes the tip cap 40 from the barrel tip 28 at an earlier station or the device 900 can be different from the device 300 so long as the device 900 is configured to grasp the tip cap 40 from the post 161 and then place the tip cap 40 back on the barrel tip 28.

Figure 7:
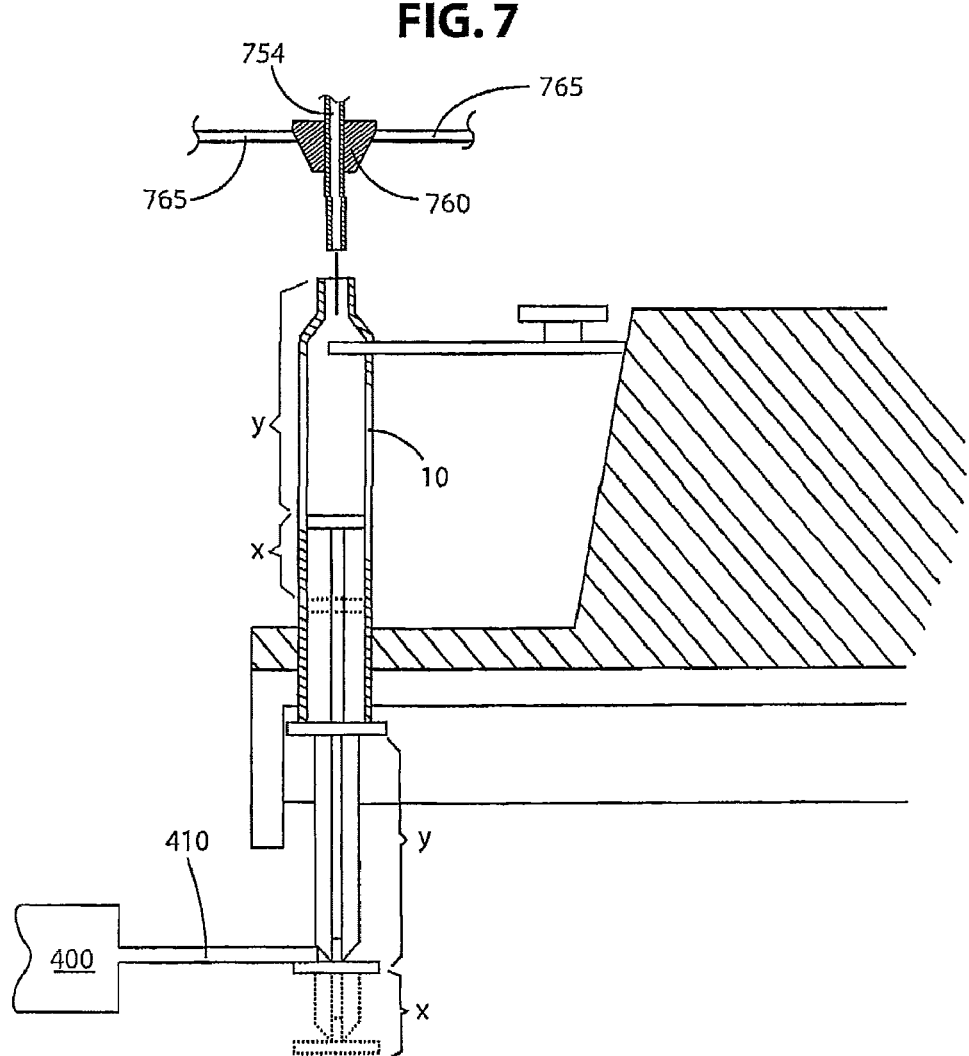
FIG. 7 is a cross-sectional view of a syringe being held with a plunger thereof being extended by an automated plunger extension mechanism.

It will be appreciated, and as described above, that the system 100 and in particular, the reservoir mode station 770 thereof, is configured to perform multiple plunger extension operations (sequential plunger extensions) as illustrated in FIG. 7. For example, the syringe 10 is delivered to the station 770 in an empty form and then the device 400 engages the plunger 50 and based on instructions and commands received from the master controller, the device 400 extends the plunger 50 a first predetermined distance (distance Y in FIG. 7) to draw in a prescribed amount of a first fluid from a first fluid dispensing mechanism, such as device 400, and then once the prescribed amount of first fluid is delivered into the syringe 10, the device 400 operates to extend the plunger 50 a second predetermined distance (distance X in FIG. 7) that corresponds to a load volume or space that is intended to receive a second fluid from a second fluid dispensing mechanism which is different from the first fluid dispensing mechanism. Typically, the second fluid dispensing mechanism is located downstream of the first fluid dispensing mechanism and is configured to be able to reconstitute the medication. The first fluid dispensing mechanism is preferably a device that is not of the type that reconstitutes medication but instead, is of a type that can deliver the first fluid (e.g., diluent for diluting a drug) in a pumpless manner and the second fluid dispensing mechanism delivers the second fluid without means of extending the plunger of the syringe.

While, in one embodiment, the extension of the plunger 50 is controlled to a high degree of precision by using a servo motor (e.g., stepper motor) that is operated to cause movement of the plunger the precise distance which results in the proper amount of fluid being drawn into the syringe, other mechanisms are available to perform the same function. In particular, a laser unit can be provided and positioned so that a laser beam generated thereby is positioned and set to the fluid level desired and then the fluid is added to the syringe until the laser beam is broken at which time, the delivery of the fluid is stopped. Both methods provide precise manners for delivering a prescribed, precise volume of fluid to the syringe.

The first fluid is preferably a diluent that dilutes the drug concentration in the second fluid to produce a final drug product that has the precise concentration of medication. However, it will also be understood that the first and second fluids contain two different drugs and therefore, the final drug product is a combination of two drugs that are drawn from two separate sources by means of extension of the plunger.

The capped syringe 10 can then be transferred to other stations, such as a station where the syringe in bandolier form is cut into individual syringes 10 that are labeled for particular patients. The syringes 10 can then be unloaded from the dial 130 and then further processed, as for example, by being delivered to a storage receptacle where it is stored or by being delivered to a transporting device for delivery to the patient or the filled syringes 10 can be cataloged and packaged in different boxes or the like for delivery to one more locations. For example, in a batch type process, which is typically more common with the reservoir mode type of operation, a number of syringes 10 can be prepared and delivered into a single box or receptacle.

In yet another aspect of the present invention illustrated in FIGS. 10-12, the system 100 includes software that permits the user to enter (input) drug vial information which is then used to calculate and control the movement and position of the vented cannula 610 with respect to a septum 61 of the drug vial 60. As previously mentioned, the vented cannula 610 includes the drug delivery cannula portion and a separate air vent channel that terminates in a vent port proximate the open cannula portion. In order for the vent portion to be in an active, open position, the vent port must be positioned within the interior chamber of the drug vial 60 below the septum 61 so as to permit atmospheric air to travel into the interior chamber (i.e., the interior is vented), thereby allowing fluid (e.g., diluent) to be injected into the interior chamber or reconstituted medication to be aspirated therefrom. It will be appreciated that if the vent port is not positioned within the interior chamber, then the vent feature is not active and diluent cannot be easily added to the drug vial 60 to reconstitute the medication and reconstituted cannot be easily aspirated from the interior chamber.

Thus, in order for the vent feature to be active, the cannula 610 must be positioned so that the vent port clears the septum and is positioned below the septum 61 inside the interior chamber.

There are a number of different vial types 60 that are commercially marketed by a number of different manufacturers. Not only do drug vials 60 come in different sizes (e.g., different volume sizes) and shapes, but also, the drug vials 60 have different septum types 61. For example and importantly, the thickness of the septum 61 can vary from one application to another (e.g., from one vial 60 to another vial 60). Thus, if the thickness of septum A is 5 units and the thickness of the septum B is 10 units, the computer control system and positioning system of the drug delivery device and in particular, the cannula control unit, must take this difference into account into to properly position the vent in the correct location where it is active. For example, if the control system simply moved and positioned the cannula in the same position for the septums A and B, the vent port may clear the septum A but in the case of septum B, the vent port may not clear the lower surface of the septum 61 but instead is located within the septum 61 itself and thus, be in an inactive or closed position. Thus, it is clearly desirable for the control and positioning system to be able to recognize the type of septum 61 that is being used with the particular drug vial 60 that is being operated on by the system 100.

In accordance with one embodiment of the present invention, the software of the control and positioning system includes a database that stores pertinent information about the drug vial and in particular, pertinent information about the septum 61. As shown in FIG. 16, the computer screen 1100 can include a number of input boxes in which the operator can enter certain vial characteristics, such as the vial width, height, and septum distance (thickness). The database can store the dimensions of the septum 61, especially, the thickness of the septum 61. This stored information is used to control the positioning of the cannula 610 and in particular, to control the precise location of the open tip and vent port of the cannula 610 with respect to the septum contained in the drug vial 60.

More specifically and during the initial input of information (e.g., using a keyboard, etc.), the user can enter not only information about the drug product order but also information about the drug vial 60. For example, the user can enter that the drug vial 60 is a 50 ml vial type X from company Y. Alternatively, the type of drug vial 60 can be inputted by means of scanning the barcode or the like that is contained on the drug vial 60. In the embodiment, the initial scan of the barcode transfers to the master controller not only information about the contents of the drug vial 60 but also transfers to the master controller information about the drug vial type.

Once the master controller receives the inputted or read information about the vial type, the master controller searches the database for this particular vial type and once it is found in the database, the related stored information in the database is retrieved and is used to control the positioning of the cannula unit. In particular, the dimensions, and particularly, the thickness and diameter of the septum 61, are used in the calculation of how far the cannula is lowered with respect to the drug vial 60 so as to ensure that not only the open drug delivery portion of the cannula 610 but also the vent port of the cannula 610 completely clear the septum so that both of these features are positioned within the interior chamber of the drug vial 60 (FIG. 12). This results in the vent port being in an active position to ensure proper venting of the interior chamber of the drug vial 60 to atmospheric air to permit either diluent to be added to the drug vial 60 to reconstitute the medication or the aspiration of the fluid (e.g., reconstituted medication) from the drug vial 60.

Accordingly, by accessing the vial characteristics stored in memory based on the inputted or read vial identifying information, the computer system determines a precise load location where the vent port is open (active venting) by being located completely within the interior chamber below the septum 61 as in FIG. 12 and a second position where the vent port is closed as in the case where venting of the interior chamber is not desired as in FIG. 11. The computer software can use a coordinate mapping system or other drive technology to position the cannula with preciseness at one of these positions. This permits the position of not only the open end tip of the cannula, but also the vent port, to be tracked at all times relative to the septum 61 since the thickness of the septum 61 is stored in the database and thus, it can easily be calculated the precise location where the cannula tip needs to be driven in order to clear the septum 61 and similarly, the location that the vent port needs to be driven to in order to clear the septum 61 and be engaged (open or active).

It will be appreciated that the above process is not limited to the use of the vented cannula 610 but applies instead to the use of any vented instrument, such as a vented syringe tip, etc.

In another aspect, the stored vial characteristic information can contain information about the angle draw of the fluid (reconstituted medication) contained in the vial 60. For example, different septum designs have different preferred positions of an angle of drawing the reconstituted medication from the drug vial interior. For example, one draw angle is 90 degrees in which the cannula 610 is inserted through the septum 61 at a 90 degree angle and then the medication is drawn through the cannula 610 from the interior chamber. If the draw angle is 45 degrees for a particular vial and septum 61, then the cannula 610 is inserted through the septum 61 and the vial 60 (with cannula) is rotated to a 45 degree angle relative to a ground surface, etc. The reconstituted medication is then drawn from the vial 60 at this angle.

Once again, it will be appreciated that in a typical drug drawing operation, the vented needle 610 (cannula) is placed in a multitude of positions in order to optimize the amount of drug that is being drawn from the vial 60. For example, in the initial drug drawing operation, the vent is engaged by clearing the septum 61 to permit the medication (e.g., reconstituted medication) to be drawn from the drug vial 60. The computer system can be programmed so that once a substantial amount of the drug has been drawn and only a small amount remains in the vial 60, the vent is not engaged to permit the last small amount of drug to be drawn from the vial 60. In other words, the automated positioning system (e.g., coordinate tracking system) can be used to position the tip of the cannula just through the septum 61 in order to get every last drop of medication from the vial 60.

In addition, the repeated piercing of the septum 61 in the same location by the cannula 610 can cause coring to occur due to the exposed septum being repeatedly penetrated at the same location which causes small pieces of the rubber septum 61 to dislodge. This is especially the case for multi-dose vials 60 that are used multiple times. To prevent coring of the septum 60, the system 100 can include a multi-position septum penetration feature in which software records, stores and controls the location where the piercing object (such as cannula 610 or a needle of the syringe 10) pierces the septum 61. As previously described and in the case of the cannula unit 590, for example, a master controller controls the movements of the cannula unit 590 and in particular, controls the vertical motion of the cannula unit 590 so that the cannula 610 is delivered to the correct location inside the vial 60 and relative to the septum 61. However, in order to eliminate the coring problem, the master controller is configured to control the entry point or location of the entry of the piercing object into the septum 61. In other words, the same location of the septum 61 is not repeatedly pierced by the inserted object but instead, the cannula unit 590 is controlled so that the unit 590 moves laterally relative to the septum 61 to cause the cannula 610 to enter a different location of the septum 61.

For example, the software associated with the master controller can contain a program and a database that keeps track of the prior locations where a particular vial that is uniquely identified has been pierced and it also contains a stored piercing pattern that includes multiple piercing points that have different mapped coordinates so that they do not overlie one another and therefore, successive piercings of the same septum 61 result in the piercing object contacting and entering different locations (coordinates) of the septum 61 as illustrated in FIG. 10. Thus, as soon as the multi-use drug vial 60 is identified by its unique identifier (e.g., a barcode, RFID, etc.), the controller accesses the database and retrieves the stored past history of the septum piercing locations for this particular septum 61 and then, it determines the next piercing location and instructs the fluid delivery unit to move the piercing object to that location. As viewed from the top, the septum can be pierced in a number of randomly scattered locations. In another example, the master controller uses the information about the material characteristics of the septum of a given vial in the database, and adjusts the speed of insertion of cannula through the septum. In other words, the master controller can control the cannula so that it has a relatively faster speed to penetrate a hard septum to minimize coring.

Figure 13:
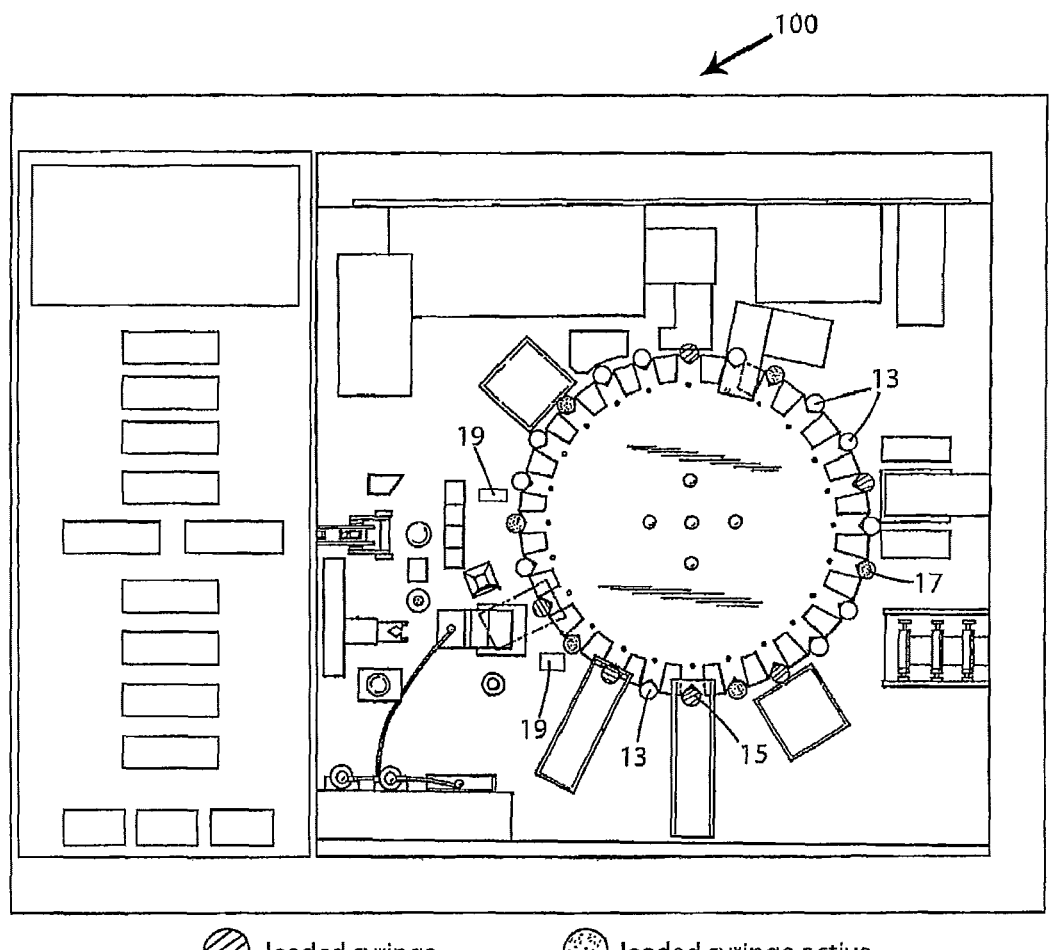
FIG. 13 is a computer screen image of the system of FIG. 2 with indicia representing loaded stations and empty station and active and inactive stations.

In yet another feature of one embodiment of the present invention, the system 100 can include software that includes a computer display that permits the operator to easily determine at any given time the location and status of each syringe 10 as it advances through the automated system as illustrated in FIG. 13. In particular, the system 100 has a video display 1001 that displays the movements of the components of the system 100 in real time so that the user can monitor and track the drug delivery devices (e.g., syringes or bags) as they are advanced from one station to a next station. For example, the system 100 typically includes a keyboard or pad or the like that permits the operator to input certain data, such as, the drug order contents, the drug vial information, etc., and it includes a display or monitor that permits the operator to graphically view all this information in real time.

FIG. 13 is a screen shot or image of an exemplary video display in which the various stations of the system 100 are identified, as well as the conveyor or transporter (in this case, the dial 13), that moves the drug delivery devices. In particular, the precise locations of the syringes around the dial 130 are indicated by a closed circle outline 13 in FIG. 13, however, it will be appreciated that other shapes can equally be used to illustrate the location of the syringes 10. As will be appreciated, these circle outlines 13 represent pockets or nests around the dial 130 where the syringes 10 are inserted and held in place as the dial 130 is advanced to move the syringes from one location to another location.

If a particular pocket or nest is empty and does not include a syringe 10, then the circle outline 13 at this location remains empty and is not "filled" with color so as to indicate the presence of a syringe 10. When a syringe 10 is fed into and held within a particular pocket or nest, the circle is shown as a filled circle 15 of any given first color. In this manner, the empty circle identifiers 13 around the dial 130 represent areas where no syringe is present and the filled circle 15 identifiers represent locations where syringes 10 are present.

In another aspect, the color of the filled circles 13 can change based on whether the syringe that is located at this particular location is undergoing some type of operation and is thus, at an active station or whether, the syringe 10 at this location is inactive and is waiting to be advanced to a next station where an operation is to be performed. For example, a loaded inactive syringe 10 can be identified on the screen by a blue colored circle 15 and when this loaded syringe 10 is advanced to an active station where some type of operation is performed on the syringe (e.g., decapping of the syringe, filling or aspiration of medication, etc.), the color of the circle 13 changes from blue to green to indicate that this particular syringe is at an active station and is being subjected to some type of operation. This is represented as a green colored circle 17. As soon as the operation has stopped, the color of the circle 13 returns back to blue to indicate an inactive site.

It will also be appreciated that each syringe 10 can be identified by a tag 19 on the display screen that contains a unique identifying code to permit the operator to easily and quickly determine which syringe 10 is located at each station. For example, the tag 19 can be visual tag that is displayed on the screen next to the circle 13 that identifies a loaded syringe and as the transporter (dial) is advanced, the tag 19 moves along with the depiction of the syringe (e.g., the filled-in circle identifier). The unique identifying code can be chosen by the computer software and linked to the syringe barcode, etc., or the identifying code can be the barcode itself.

In contrast to conventional automated syringe handling systems, the system 100 is not restricted to being operated in a sequential manner where one syringe is fed from one station to the next but instead, the system 100 is configured so that there can be a number of active work stations performing some type of automated operation at the same time. Thus, at any given time, the video display can show two or more green colored syringe identifiers to indicate that two or more syringes are at active stations where work is occurring. For example, in the serial dilution mode of operation, both the reservoir mode station 770 and the fluid transfer station 170 can be and preferably are active at any one point in time and therefore, the visual syringe identifiers at these two stations will be colored green on the visual display to show that work is being performed on these syringes at the given stations. In addition, one syringe may be undergoing a decapping operation at station 150, while at the same time, another syringe is receiving a dosage of medication at the fluid transfer station 170 and therefore, the visual syringe identifiers for these two syringes will be green colored. It will be appreciated that there is no limit as to the number of stations that can be active at the same point in time and therefore, in contrast, to conventional design, the present invention is a multi-station operation that is not limited to being a sequential operation where a gripper or robotic device delivers one syringe from one station to another station until all operations have been performed on the syringe and then at that point in time, the robotic device will get another empty syringe and start the sequential process over. However, this type of process is a sequential process where only after work is completed on one syringe does work start on the next syringe.

Figure 9:
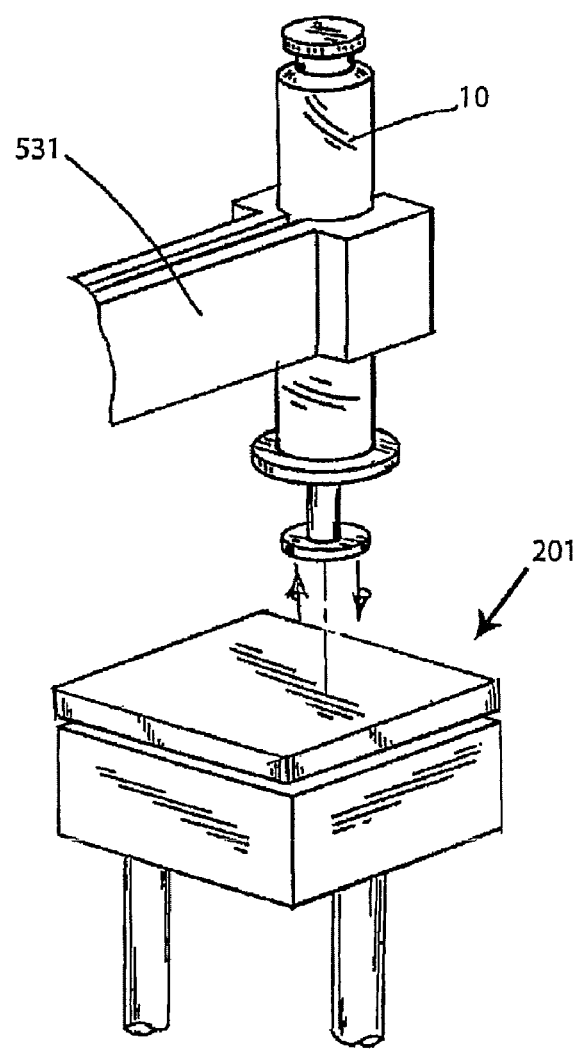
FIG. 9 is a partial perspective view of a robotic device holding a syringe and a weigh station for weighing a filled syringe.

In yet another safety feature of the present invention illustrated in FIGS. 2 and 9, syringes that are present at a set interval are removed from the dial 130 just prior to the unloading station 200 and are delivered via a robotic device 531 to a weigh station 201 where the filled syringe is weighed. For example, every $10^{th}$ syringe or some other syringe interval can be removed from the dial 130 and delivered to the weigh station 201. The filled syringe 10 is then checked with a stored value (target value) and if it is within a range of accepted values, the syringe is then delivered back to the unloading station where it is then removed from the dial 130 and placed on a conveyor or the like. This safety feature is particularly useful and is intended for use more when a batch of syringes having the same specifications is prepared since checking syringes at predetermined intervals is a quality control measurement for checking the integrity and precision of the batch filling devices.

The software can be configured so that if one of the selected syringes has a weight that is outside of the acceptable range, then not only is this particular syringe discarded but the operator can be given several safety feature options, including, modifying the interval at which the syringes are checked so that the interval is decreased (e.g., instead of checking every $10^{th}$ syringe, the system can be modified to check every $3^{rd}$ syringe, etc.); the operator can undertake a check of the filled syringes that exited the system 100 for a given preceding time period; etc.

As shown in FIG. 1, the system 100 is typically incorporated into the housing 1300, such as a cabinet, that has different compartments for storing the components of the system 100. For example and as shown in FIG. 1, the housing can include a first space 1310 in the form of the drug cabinet 110 that stores the drug vials 60 (FIG. 6), as by storing them vertically in a number of different rows. The drug cabinet 110 preferably includes sensors and the like for indicating when a row of drug vials 60 is low or has run out. The mechanism 510 (FIG. 2) that transports an individual drug vial 60 from the drug cabinet 110 to the other working components that are located in a second space 1320 of the housing 1300 is located along one side of the housing 1300.

The other working components of the system 100 that are disposed in the second space 1320 are accessible through one or more side windows 1322 and preferably, each side of the housing 1300 includes slideable doors or windows 1322. When the doors 1322 are shut, the interior of the housing 1300 is sealed. Since a number, if not all, applications, especially, the preparation of chemotherapy drugs, require a sterile environment, the housing 1300 includes one or more filters 1332 and in particular, one or more HEPA filters 1332 (high efficiency particulate absorbing filters) that are typically designed to remove at least 99.97% of dust, pollen, mold, bacteria and any airborne particles with a size of 0.3 micrometers at 85 liters per minute.

In one embodiment, the housing 13000 has the HEPA filtration system 1332 incorporated into a ceiling or roof 1340 of the housing 1300 and includes one or more HEPA filters 1332. The HEPA filter 1332 functions to filter air that enters the cabinet by any number of different means, including the opening of one glass door 1322. The HEPA filtration system 1332 also includes at least one and preferably a plurality of sensors/sensing devices, such as particulate sensors, 1350 that continuously monitor the conditions inside the housing 1300 and more specifically, measure the level of particulates within the housing 1300. The sensors 1350 can be placed in a number of different target locations within the housing 1300. For example, one sensor 1350 can be located on the ceiling/roof, one can be located on a side wall of the housing, one can be located on a floor of the second space, etc.

The sensors 1350 communicate with the master controller which is configured to continuously monitor the readings from the sensors and if one reading, such as particulate count, is outside an acceptable range, then the master controller takes appropriate action which can be to alert the operator and/or take remedial action in an attempt to correct the matter. For example, the alert can be in the form of an alarm (audible and/or visual) that alerts the operator that an error or undesired condition exists in the housing or with the system 100. The alert can also be in the form of a text message, such as an email, that is sent to one or more recipients to alert them of the current unacceptable condition. Conventional wireless or wired communications equipment can be provided to perform this function.

The alert functionality and error display functionality is not limited to instances where a high particulate count is observed but it can be a result of any other type of error situation, including a jam at the loading station 120 or that the machine has run out of a feed of syringes 10 or a jam has occurred at another station or a measured parameter is outside an acceptable range.

In one embodiment, the housing 1300 includes a visual alert device 1352, such as a flashing light or solid color light, that is positioned near the top of the housing so that anyone in the area of the housing 1300 can see when it is activated and is flashing to alert the operator to check the visual display (computer monitor) for an error message that details what problem or error has been detected. For example, during normal operation, the light 1352 is a green color; however, when there is a problem or error, the light 1352 has a red color and can also blink, etc., or remain a solid color.

Once the light 1352 flashes, the operator can ascertain the reason for the activation of the light by looking at the computer screen since preferably, there is a section (e.g., a lower portion of the screen) that lists any current error message. For example, the display could indicate "Error Message 002—Jam at Syringe Feed Station" or "Error Message 005—High Particulate Reading at Sensor 001" or "Error Message 006—Syringe Cap not detected at Station 0033," etc. Proper remedial action can then be taken.

In yet another safety feature, the drug cabinet 110 can be constructed so that is can receive a cleaning solution that is intended to decontaminate the drug cabinet 110. For example, any wiring that is exposed in the drug cabinet 110 can be routed through protective sleeves or is otherwise protected and the drug cabinet 110 can include one or more devices that are intended to dispense fluid in a controlled manner through the drug cabinet, including the drug vials 60, contained therein. For example, the devices can be in the form of misting devices or sprayers that are fluidly connected to both a source of decontaminating fluid and a controller that controls the dispensing of the fluid. The controller is operatively connected to the master controller (computer) and therefore is a programmable device that can be programmed to dispense fluid at regular intervals. For example and depending upon applicable regulatory requirements, the controller can be set up to cause a spraying of decontaminating fluid within the drug cabinet 110, including over the stored drug vials 60, at a precise time interval, such as daily, weekly, monthly, etc. and for a programmable amount of time.

Any number of different decontaminating fluids can be used with one exemplary embodiment being alcohol.

The drug cabinet 110 can thus contain a drain or the like to collect any decontaminating fluid that may have run off the equipment in the drug cabinet, including the vials. The drain can then lead to a waste receptacle.

It will be appreciated by persons skilled in the art that the present invention is not limited to the embodiments described thus far with reference to the accompanying drawings; rather the present invention is limited only by the following claims.

What is claimed is:

1. An automated device for removing a tip cap from an empty syringe, placing the tip cap at a remote location, and replacing the tip cap on a filled syringe, the tip cap having a base portion and a flange, the device comprising:
    a support frame that is movable along at least an x axis and a y axis;
    a gripper mechanism movable by the support frame including a pair of gripper arms at first and second locations, respectively, that are positionable between an open position and a closed position in which the base portion of the tip cap is securely held in contact therebetween during both removal of the tip cap from the empty syringe at the first location and during the subsequent replacement of the tip cap on the filled syringe at the second location, wherein the tip cap is released from the gripper mechanism between its removal and replacement after the tip cap is placed at the remote location;
    a programmable controller in communication with a plurality of drive actuators that controllably drive the gripper arms and the support frame to desired positions; and
    a sensor for detecting whether the tip cap is disposed between the gripper arms;
    whereby the gripper mechanism is available for one or more operations between the removal and replacement of the tip cap while the tip cap remains at the remote location.

2. The automated device according to claim 1, wherein the gripping mechanism having the pair of gripper arms comprises: a first automated gripping device for removing a tip cap from a barrel tip of one syringe and placing the removed tip cap at a first location; and a second automated gripping device for replacing the removed tip cap on the syringe barrel after medication has been injected therein, wherein each of the first and second automated gripping devices is in communication with the programmable controller and each of the first and second gripping devices moves in at least two directions contacts and holds the same tip cap.

3. The automated device according to claim 2, wherein the second automated gripping device is located at a different location than the first automated gripping device, the syringe being held in a fixed position as is advanced from the first automated gripping device to the second automated gripping device.

4. The automated device according to claim 2, further including a station where a plunger of the syringe is extended prior to filling the syringe at another station, the syringe being advanced to the station where the plunger is extended after the first automated gripping device removes the tip cap.

5. The automated device according to claim 4, further including an automated rotary device that receives and holds a plurality of syringes in a nested manner and is indexed to advance one syringe from one station to another station including stations where the first automated gripping device is located, the plunger is extended and the second automated gripping device is located.

6. The automated device according to claim 1, wherein each of the gripping arms has a platform with a shaped cut out formed at one edge thereof and the two shaped cut outs are aligned with one another so that when the gripper arms are in the closed position, the shaped cut outs define an opening that is sized to receive and hold the tip cap.

7. The automated device according to claim 1, wherein each of the first and second automated gripper arms is movable along an x axis and a y axis.

8. The automated device according to claim 1, wherein the plurality of drive actuators has a first control mechanism for controlling opening and closing of gripper arms that grasp and retain the tip cap; a second control mechanism for controlling up and down movement of the gripper arm and a third control mechanism for controlling inward and outward movement of the gripper arm.

9. The automated device according to claim 8, wherein each of the first, second and third control mechanisms is a pneumatic device that upon actuation causes movement of the device in at least one direction.

10. The automated device according to claim 8, wherein each of the first and second automated gripper arms includes a vertical base with the gripper arms being disposed closer to an upper end of the vertical base, the second control mechanism operatively connected to the vertical base to cause controlled up and down movements thereof; the third control mechanism operatively connected to the vertical base to cause controlled inward and outward movements thereof.

11. The automated device according to claim 10, wherein the second and third control mechanisms are one of pneumatic devices and mechanical motorized devices that each moves the vertical base between two positions.

12. The automated device according to claim 8, wherein the gripper arm is positionable between a starting position, a second position where the tip cap is grasped by the gripper arms for removal from the syringe, and a third position where the tip cap is disposed over a post for retainingly parking the tip cap, the post being separate from the gripping mechanism, the tip cap being inserted onto the post such that it stands upright thereon and is parked at the remote location and is free of contact with the gripping mechanism when parked at the remote location.

13. The automated device according to claim 12, further comprising a device for holding the syringe in an upstanding position while the gripper mechanism engages the tip cap, wherein the post that is formed as part of the support for receiving and holding the removed tip cap is located proximate the upstanding syringe, both the device that holds the syringe and the post being indexed to advance the syringe from one station to another station.

14. The automated device according to claim 1, further including an automated rotary device that receives and holds a plurality of syringes in discrete locations and is indexed to advance each syringe from one station to another station, the rotary device having an upstanding post for holding the removed tip cap as each syringe is advanced from one station to the next, each held syringe having a corresponding post for holding the tip cap that corresponds therewith.

15. The automated device according to claim 1, wherein the support frame comprises a vertical base that is operatively connected to a first control unit that moves the vertical base in a track along the y axis between inward and outward positions and a second control unit that moves the vertical base along the x axis between raised and lowered positions.

16. The automated device according to claim 1, wherein the gripper mechanism is operatively connected to a control unit that positions the gripper arms between the open and closed positions.

17. The automated device according to claim 1, wherein the sensor comprises a reflecting light emitting diode (LED).

18. The automated device according to claim 1, wherein the sensor is of a type that emits a light beam and a reflector is provided across from the sensor for reflecting the light beam, the sensor device being mounted relative to gripper arms that grasp and retain the tip cap so that the light beam passes through a space between the gripper arms where the tip cap is received, the sensor device in communication with the programmable controller so that a control signal is delivered to the programmable controller when the tip cap is disposed within the space, thereby impinging the light beam.

19. The automated device according to claim 1, wherein the plurality of drive actuators comprises a first pneumatic control device for controllably moving the support frame along the y axis and a second pneumatic control device for controllably moving the support frame along the x axis.

20. The automated device according to claim 1, wherein the plurality of drive actuators comprises a first motorized mechanical device mechanism for controllably moving the support frame along the y axis and a second motorized mechanical device mechanism for controllably moving the support frame along the x axis.

21. The automated device according to claim 1, wherein the support frame comprises a vertical base.

22. The automated device according to claim 1, further comprising a filling station, wherein the controller and sensor are configured such that if the sensor detects that the tip cap is not securely attached to a barrel of the syringe, then the syringe is rejected and is not filled at the filling station, and if the sensor device detects the presence of a tip cap, then the syringe is advanced, in an indexed manner, to the filling station and subjected to at least one device for automatically removing, parking the tip cap, filling the syringe and replacing the tip cap.

23. The automated device of claim 1, wherein the sensor is configured and located such that the sensor detects whether the tip cap is securely held between the gripper arms as the tip cap is both removed from the empty syringe and delivered to the remote location and as the tip cap is removed from the remote location and delivered to the filled syringe where it is placed thereon.

24. The automated device according to clam 1, further including a device for holding the syringe in an upstanding position while the gripper mechanism contacts the tip cap and the remote location includes a post on which the tip cap is placed, the post being located adjacent the upstanding syringe, both the device that holds the syringe and the post being indexed in unison to advance the syringe from one station to another station.

25. The automated device according to claim 1, wherein each gripper arm has a gripping section with a notch that receives the tip cap and has locating posts that ensure that the tip cap remains in a desired gripping position, the tip cap being disposed between a bottom face of the locating posts and an upper face of the gripping sections.

26. The automated device according to claim 1, further including an automated rotary device that receives and holds a plurality of syringes in a nested manner and is indexed to advance one syringe from one station to another station, the empty syringe with tip cap affixed thereto being introduced to the gripper mechanism while the syringe is nested on the rotary device.

27. An automated system including an automated first device for removing a tip cap from an empty syringe, placing the tip cap at a remote location, and replacing the tip cap on a filled syringe, the first device being located at a first station and a fourth station comprising: a support frame that is movable along at least an x axis and a y axis; a gripper mechanism movable by the support frame including a pair of gripper arms that are positionable between an open position and a closed position in which the tip cap is securely held in contact therebetween during both removal of the tip cap from the empty syringe at the first station and during the subsequent replacement of the tip cap on the filled syringe at the fourth station; a programmable controller in communication with a plurality of drive actuators that controllably drive the gripper arms and the support frame to desired positions; a sensor for detecting whether the tip cap is disposed between the gripper arms; and wherein the system further includes: a third station configured to fill the syringe; a second station where a plunger of the syringe is extended prior to filling the syringe at the third station, the syringe being advanced to the second station after the automated first device removes the tip cap at the first station; and an automated rotary device that receives and holds a plurality of syringes in a nested manner and is indexed to advance one syringe from one station to another station including the first station, the second station, and the third station, the tip cap being removed and replaced while the syringe is nested within the rotary device and the plunger being extended while the syringe is nested within the rotary device.

28. An automated system including an automated first device for removing a tip cap from an empty syringe, placing the tip cap at a remote location, and replacing the tip cap on a filled syringe, the first device being located at a first station and a fourth station comprising: a support frame that is movable along at least an x axis and a y axis; a gripper mechanism movable by the support frame including a pair of gripper arms that are positionable between an open position and a closed position in which the tip cap is securely held in contact therebetween during both removal of the tip cap from the empty syringe at the first station and during the subsequent replacement of the tip cap on the filled syringe at the fourth station; a programmable controller in communication with a plurality of drive actuators that controllably drive the gripper arms and the support frame to desired positions; a sensor for detecting whether the tip cap is disposed between the gripper arms; and wherein the system further includes: a third station configured to fill the syringe; a second station where a plunger of the syringe is extended prior to filling the syringe at the third station, the syringe being advanced to the second station after the automated first device removes the tip cap at the first station; and an automated rotary device that receives and holds a plurality of syringes in a nested manner and is indexed to advance one syringe from one station to another station including the first station, the second station, and the third station, the tip cap being removed and replaced while the syringe is nested within the rotary device and the plunger being extended while the syringe is nested within the rotary device.

29. An automated device for removing a tip cap from an empty syringe, placing the tip cap at a remote location, and replacing the tip cap on a filled syringe, the tip cap having a base portion and a flange, the device comprising:
 a support frame that is movable along at least an x axis and a y axis;
 a gripper mechanism movable by the support frame including a pair of gripper arms at first and second locations, respectively, that are positionable between an open position and a closed position in which the base portion of the tip cap is securely held in contact therebetween during both removal of the tip cap from the empty syringe at the first location and during the subsequent replacement of the tip cap on the filled syringe at the second location, wherein the tip cap is released from the gripper mechanism between its removal and replacement after the tip cap is placed at the remote location, the tip cap being held at the remote location independent from and free of contact with the gripper mechanism;
 a programmable controller in communication with a plurality of drive actuators that controllably drive the gripper arms and the support frame to desired positions; and
 a sensor for detecting whether the tip cap is disposed between the gripper arms;
whereby the gripper mechanism is available for one or more operations between the removal and replacement of the tip cap while the tip cap remains at the remote location.

* * * * *